United States Patent
Clark et al.

(10) Patent No.: US 8,048,658 B2
(45) Date of Patent: Nov. 1, 2011

(54) METHOD FOR PRODUCING TERPENES AND MEP-TRANSFORMED MICROORGANISMS THEREFORE

(75) Inventors: Anthony Clark, West Windsor, NJ (US); Jérôme Maury, København (DK); Mohammad Ali Asadollahi, Lyngby (DK); Kasper Møller, Olstykke (DK); Jens Nielsen, Charlottenlund (DK); Michel Schalk, Collonges-Sous-Saleve (FR)

(73) Assignee: Firmenich SA, Geneva (CH)

( * ) Notice: Subject to any disclaimer, the term of this patent is extended or adjusted under 35 U.S.C. 154(b) by 198 days.

(21) Appl. No.: 12/279,300

(22) PCT Filed: Feb. 13, 2007

(86) PCT No.: PCT/IB2007/050474
§ 371 (c)(1), (2), (4) Date: Oct. 15, 2008

(87) PCT Pub. No.: WO2007/093962
PCT Pub. Date: Aug. 23, 2007

(65) Prior Publication Data
US 2009/0155874 A1    Jun. 18, 2009

(51) Int. Cl.
C12P 5/00     (2006.01)
C12N 1/19     (2006.01)
C12N 1/63     (2006.01)
C07C 403/00   (2006.01)

(52) U.S. Cl. ............... 435/166; 435/254.21; 435/471; 585/355; 558/875

(58) Field of Classification Search .............. 435/166, 435/254.21, 471; 585/355; 558/875
See application file for complete search history.

(56) References Cited

U.S. PATENT DOCUMENTS
2004/0110257 A1   6/2004   Millis et al. ............... 435/157
2004/0176570 A1   9/2004   Bacher et al. ............. 530/350

FOREIGN PATENT DOCUMENTS
WO   WO02/18617 A2    3/2002
WO   WO02/083720 A2   10/2002
WO   WO2005/033287 A2  4/2005
WO   WO2005/079183 A2  9/2005

OTHER PUBLICATIONS

DeMarini et al. ("Constitutive promoter modules for PCR-based gene modification in Saccharomyces cerevisiae," Yeast 18:723-728, 2001).*
European Patent Convention Rule 28, Deposit of biological material, http://www.epo.org/patents/law/legal-texts/html/epc/1973/e/r28.html), printed from the Internet on Oct. 14, 2010.*
International Search Report, Application No. PCT/IB2007/050474 and Written Opinion, Oct. 15, 2007.

* cited by examiner

Primary Examiner — Rosanne Kosson
(74) Attorney, Agent, or Firm — Winston & Strawn LLP

(57) ABSTRACT

The present invention relates to a microorganism capable of producing a terpene of choice. The microorganism expresses a heterologous pathway for the formation of isoprene units and, preferably, a heterologous terpene synthase. In this way, high amounts of terpene can be isolated from the medium of the microorganism.

5 Claims, 8 Drawing Sheets

**A) Integration of the gene *lytB gcpE ispF***

**B) Integration of the gene *dxs dxr ispD ispE***

SEQUENCE LISTING

<160> NUMBER OF SEQ ID NOS: 46

<210> SEQ ID NO 1
<211> LENGTH: 31
<212> TYPE: DNA
<213> ORGANISM: Artificial
<220> FEATURE:
<223> OTHER INFORMATION: Primer dxrM1A

<400> SEQUENCE: 1
ggactagtcc taatgaagca actcaccatt c          31

<210> SEQ ID NO 2
<211> LENGTH: 29
<212> TYPE: DNA
<213> ORGANISM: Artificial
<220> FEATURE:
<223> OTHER INFORMATION: Primer dxrM1B

<400> SEQUENCE: 2
ccatcgatgg tcagcttgcg agacgcatc          29

<210> SEQ ID NO 3
<211> LENGTH: 52
<212> TYPE: DNA
<213> ORGANISM: Artificial
<220> FEATURE:
<223> OTHER INFORMATION: Primer dxsGAPs

<400> SEQUENCE: 3
actttaacgt caaggagaaa aaccccgga tcccatgagt tttgatattg cc          52

<210> SEQ ID NO 4
<211> LENGTH: 55
<212> TYPE: DNA
<213> ORGANISM: Artificial
<220> FEATURE:
<223> OTHER INFORMATION: Primer dxsGAPr

<400> SEQUENCE: 4
ttcttcggaa atcaacttct gttccatgtc gacgccttat gccagccagg ccttg          55

<210> SEQ ID NO 5
<211> LENGTH: 31
<212> TYPE: DNA
<213> ORGANISM: Artificial
<220> FEATURE:
<223> OTHER INFORMATION: Primer ispDM1A

<400> SEQUENCE: 5
ggactagtcc taatggcaac cactcatttg g          31

<210> SEQ ID NO 6
<211> LENGTH: 29
<212> TYPE: DNA
<213> ORGANISM: Artificial
<220> FEATURE:
<223> OTHER INFORMATION: Primer ispDM1B

<400> SEQUENCE: 6
ccatcgatgg ttatgtattc tcctgatgg          29

<210> SEQ ID NO 7
<211> LENGTH: 54
<212> TYPE: DNA

-continued

<213> ORGANISM: Artificial
<220> FEATURE:
<223> OTHER INFORMATION: Primer ispEGAPs

<400> SEQUENCE: 7
actttaacgt caaggagaaa aaacccggga tcccatgcgg acacagtggc cctc        54

<210> SEQ ID NO 8
<211> LENGTH: 57
<212> TYPE: DNA
<213> ORGANISM: Artificial
<220> FEATURE:
<223> OTHER INFORMATION: Primer ispEGAPr

<400> SEQUENCE: 8
ttcggaaatc aacttctgtt ccatgtcgac gccttaaagc atggctctgt gcaatgg     57

<210> SEQ ID NO 9
<211> LENGTH: 29
<212> TYPE: DNA
<213> ORGANISM: Artificial
<220> FEATURE:
<223> OTHER INFORMATION: Primer ispFM1A

<400> SEQUENCE: 9
ggactagtcc taatgcgaat tggacacgg                                   29

<210> SEQ ID NO 10
<211> LENGTH: 29
<212> TYPE: DNA
<213> ORGANISM: Artificial
<220> FEATURE:
<223> OTHER INFORMATION: Primer ispFM1B

<400> SEQUENCE: 10
ccatcgatgg tcattttgtt gccttaatg                                   29

<210> SEQ ID NO 11
<211> LENGTH: 34
<212> TYPE: DNA
<213> ORGANISM: Artificial
<220> FEATURE:
<223> OTHER INFORMATION: Primer gcpEM1A

<400> SEQUENCE: 11
ggactagtcc taatgcataa ccaggctcca attc                             34

<210> SEQ ID NO 12
<211> LENGTH: 30
<212> TYPE: DNA
<213> ORGANISM: Artificial
<220> FEATURE:
<223> OTHER INFORMATION: Primer gcpEM1B

<400> SEQUENCE: 12
cgagctcgtt atttttcaac ctgctgaacg                                  30

<210> SEQ ID NO 13
<211> LENGTH: 36
<212> TYPE: DNA
<213> ORGANISM: Artificial
<220> FEATURE:
<223> OTHER INFORMATION: Primer lytBM1A

<400> SEQUENCE: 13
gcgtcgacgt cttgatgcag atcctgttgg ccaacc                           36

<210> SEQ ID NO 14
<211> LENGTH: 33
<212> TYPE: DNA
<213> ORGANISM: Artificial
<220> FEATURE:
<223> OTHER INFORMATION: Primer lytBM1B

<400> SEQUENCE: 14
ccctcgaggg tttaatcgac ttcacgaata tcg                           33

<210> SEQ ID NO 15
<211> LENGTH: 59
<212> TYPE: DNA
<213> ORGANISM: Artificial
<220> FEATURE:
<223> OTHER INFORMATION: Primer pfus_grf

<400> SEQUENCE: 15
cagcactacc ctttagctgt tctatatgct gccactccta cgcaaaccgc ctctccccg   59

<210> SEQ ID NO 16
<211> LENGTH: 58
<212> TYPE: DNA
<213> ORGANISM: Artificial
<220> FEATURE:
<223> OTHER INFORMATION: Primer Pfus_grr

<400> SEQUENCE: 16
aggaaatgat agcattgaag gatgagacta atccaattat cggtgcgggc ctcttcgc    58

<210> SEQ ID NO 17
<211> LENGTH: 38
<212> TYPE: DNA
<213> ORGANISM: Artificial
<220> FEATURE:
<223> OTHER INFORMATION: Primer GFTpsCM2A

<400> SEQUENCE: 17
cgggatcccg tgggccctat ggcacttcaa gattcaga                      38

<210> SEQ ID NO 18
<211> LENGTH: 34
<212> TYPE: DNA
<213> ORGANISM: Artificial
<220> FEATURE:
<223> OTHER INFORMATION: Primer GFTpsCM2B

<400> SEQUENCE: 18
aagacgtcga cgcttcaaaa gggaacaggc ttct                         34

<210> SEQ ID NO 19
<211> LENGTH: 38
<212> TYPE: DNA
<213> ORGANISM: Artificial
<220> FEATURE:
<223> OTHER INFORMATION: Primer GFTpsD6M2A

<400> SEQUENCE: 19
cgggatcccg tgggccctat gtcgtctgga gaaacatt                     38

<210> SEQ ID NO 20
<211> LENGTH: 34
<212> TYPE: DNA
<213> ORGANISM: Artificial
<220> FEATURE:
<223> OTHER INFORMATION: Primer GFTpsD6M2B

```
<400> SEQUENCE: 20
aagacgtcga cgcttcaaaa tggaacgtgg tctc                          34

<210> SEQ ID NO 21
<211> LENGTH: 59
<212> TYPE: DNA
<213> ORGANISM: Artificial
<220> FEATURE:
<223> OTHER INFORMATION: Primer Ps_GAP_f

<400> SEQUENCE: 21
actttaacgt caaggagaaa aaaccccgga tccaatggag ttgtatgccc aaagtgttg   59

<210> SEQ ID NO 22
<211> LENGTH: 64
<212> TYPE: DNA
<213> ORGANISM: Artificial
<220> FEATURE:
<223> OTHER INFORMATION: Primer Ps_GAP_r

<400> SEQUENCE: 22
ttcttcggaa atcaacttct gttccatgtc gacgccttaa tatggaacag ggtgaaggta   60
caac                                                               64

<210> SEQ ID NO 23
<211> LENGTH: 20
<212> TYPE: DNA
<213> ORGANISM: Artificial
<220> FEATURE:
<223> OTHER INFORMATION: Primer Dxr_f_new

<400> SEQUENCE: 23
cagtgattca ctcaatggtg                                          20

<210> SEQ ID NO 24
<211> LENGTH: 22
<212> TYPE: DNA
<213> ORGANISM: Artificial
<220> FEATURE:
<223> OTHER INFORMATION: Primer Dxr_r_new

<400> SEQUENCE: 24
acgcatcacc tcttttctgg cg                                       22

<210> SEQ ID NO 25
<211> LENGTH: 22
<212> TYPE: DNA
<213> ORGANISM: Artificial
<220> FEATURE:
<223> OTHER INFORMATION: Primer lytB_f

<400> SEQUENCE: 25
ctggcagaac aggcggaagt tg                                       22

<210> SEQ ID NO 26
<211> LENGTH: 21
<212> TYPE: DNA
<213> ORGANISM: Artificial
<220> FEATURE:
<223> OTHER INFORMATION: Primer lytB_r

<400> SEQUENCE: 26
acgcagctct ttcggcactt c                                        21

<210> SEQ ID NO 27
```

```
<211> LENGTH: 20
<212> TYPE: DNA
<213> ORGANISM: Artificial
<220> FEATURE:
<223> OTHER INFORMATION: Primer ispF_f

<400> SEQUENCE: 27
gctccatgcg ttgaccgatg                                              20

<210> SEQ ID NO 28
<211> LENGTH: 22
<212> TYPE: DNA
<213> ORGANISM: Artificial
<220> FEATURE:
<223> OTHER INFORMATION: Primer ispF_r

<400> SEQUENCE: 28
ccggtaaatc ccagttttc cg                                            22

<210> SEQ ID NO 29
<211> LENGTH: 22
<212> TYPE: DNA
<213> ORGANISM: Artificial
<220> FEATURE:
<223> OTHER INFORMATION: Primer ispE_f

<400> SEQUENCE: 29
taaagatcct gaactcccgc gc                                           22

<210> SEQ ID NO 30
<211> LENGTH: 20
<212> TYPE: DNA
<213> ORGANISM: Artificial
<220> FEATURE:
<223> OTHER INFORMATION: Primer ispE_r

<400> SEQUENCE: 30
catggctctg tgcaatgggg                                              20

<210> SEQ ID NO 31
<211> LENGTH: 21
<212> TYPE: DNA
<213> ORGANISM: Artificial
<220> FEATURE:
<223> OTHER INFORMATION: Primer ispD_f

<400> SEQUENCE: 31
cgcaccagtg cgcgatacta t                                            21

<210> SEQ ID NO 32
<211> LENGTH: 22
<212> TYPE: DNA
<213> ORGANISM: Artificial
<220> FEATURE:
<223> OTHER INFORMATION: Primer ispD_r

<400> SEQUENCE: 32
cctgatggat ggttcgggtg ag                                           22

<210> SEQ ID NO 33
<211> LENGTH: 20
<212> TYPE: DNA
<213> ORGANISM: Artificial
<220> FEATURE:
<223> OTHER INFORMATION: Primer gcpE_f

<400> SEQUENCE: 33
```
aacttcatcg cctgcccgac                                               20

<210> SEQ ID NO 34
<211> LENGTH: 20
<212> TYPE: DNA
<213> ORGANISM: Artificial
<220> FEATURE:
<223> OTHER INFORMATION: Primer gcpE_r

<400> SEQUENCE: 34
caattcgacg cgcttcgtcc                                               20

<210> SEQ ID NO 35
<211> LENGTH: 21
<212> TYPE: DNA
<213> ORGANISM: Artificial
<220> FEATURE:
<223> OTHER INFORMATION: Primer dxs_f

<400> SEQUENCE: 35
tgatgccaga agcggcgaaa g                                             21

<210> SEQ ID NO 36
<211> LENGTH: 20
<212> TYPE: DNA
<213> ORGANISM: Artificial
<220> FEATURE:
<223> OTHER INFORMATION: Primer dxs_r

<400> SEQUENCE: 36
ttggcttcca taccagcggc                                               20

<210> SEQ ID NO 37
<211> LENGTH: 20
<212> TYPE: DNA
<213> ORGANISM: Artificial
<220> FEATURE:
<223> OTHER INFORMATION: Primer Actin_forward

<400> SEQUENCE: 37
gccggtattg accaaactac                                               20

<210> SEQ ID NO 38
<211> LENGTH: 20
<212> TYPE: DNA
<213> ORGANISM: Artificial
<220> FEATURE:
<223> OTHER INFORMATION: Primer Actin_reverse

<400> SEQUENCE: 38
ggtgatttcc ttttgcattc                                               20

<210> SEQ ID NO 39
<211> LENGTH: 19
<212> TYPE: DNA
<213> ORGANISM: Artificial
<220> FEATURE:
<223> OTHER INFORMATION: Primer ERG13up_f

<400> SEQUENCE: 39
gacgaactgg atgagatgg                                                19

<210> SEQ ID NO 40
<211> LENGTH: 39
<212> TYPE: DNA
<213> ORGANISM: Artificial
<220> FEATURE:

```
<223> OTHER INFORMATION: Primer ERG13up_Pr-b

<400> SEQUENCE: 40
gatccccggg aattgccatg gagagtttca tgctgcacc                                    39

<210> SEQ ID NO 41
<211> LENGTH: 41
<212> TYPE: DNA
<213> ORGANISM: Artificial
<220> FEATURE:
<223> OTHER INFORMATION: Primer Pr-b-KL

<400> SEQUENCE: 41
catggcaatt cccggggatc gtgattctgg gtagaagatc g                                 41

<210> SEQ ID NO 42
<211> LENGTH: 25
<212> TYPE: DNA
<213> ORGANISM: Artificial
<220> FEATURE:
<223> OTHER INFORMATION: Primer 5'int

<400> SEQUENCE: 42
cttgacgttc gttcgactga tgagc                                                   25

<210> SEQ ID NO 43
<211> LENGTH: 44
<212> TYPE: DNA
<213> ORGANISM: Artificial
<220> FEATURE:
<223> OTHER INFORMATION: Primer dKl3'

<400> SEQUENCE: 43
gtcagcggcc gcatccctgc cctcactaaa gggaacaaaa gctg                              44

<210> SEQ ID NO 44
<211> LENGTH: 25
<212> TYPE: DNA
<213> ORGANISM: Artificial
<220> FEATURE:
<223> OTHER INFORMATION: Primer 3'int

<400> SEQUENCE: 44
gagcaatgaa cccaataacg aaatc                                                   25

<210> SEQ ID NO 45
<211> LENGTH: 41
<212> TYPE: DNA
<213> ORGANISM: Artificial
<220> FEATURE:
<223> OTHER INFORMATION: Primer ERG13dw_dKl3'

<400> SEQUENCE: 45
gcagggatgc ggccgctgac cgattgcatc ttgctgaacc c                                 41

<210> SEQ ID NO 46
<211> LENGTH: 19
<212> TYPE: DNA
<213> ORGANISM: Artificial
<220> FEATURE:
<223> OTHER INFORMATION: Primer ERG13_dw_r

<400> SEQUENCE: 46
ccagaggtca aattccctc                                                          19
```

METHOD FOR PRODUCING TERPENES AND MEP-TRANSFORMED MICROORGANISMS THEREFORE

This application is a 371 filing of International Patent Application PCT/IB2007/0050474 filed Feb. 13, 2007.

TECHNICAL FIELD

The present invention relates to microorganisms having a heterologous pathway for producing isopentenyl diphosphate and/or dimethylallyl diphosphate, and to a method for accumulating a terpenoid in a cell and/or a medium.

BACKGROUND ART

Isoprenoids (also known as terpenoids or terpenes) are a large, diverse group of complex natural products with considerable commercial interest. Isoprenoids are today mostly extracted from plants or chemically synthesized to be used as pharmaceuticals (e.g. taxol, bisabolol, lycopene, artemisinin), animal feed supplements and food colorants (various carotenoids) or flavours and fragrances (e.g. menthol, patchoulol, nootkatone). Isoprenoids are built from isoprene units (2-methyl-1,3-butadiene), and the biological precursor for all natural isoprenoids is isopentenyl diphosphate (IPP). Isoprenoids play important roles in living cells, such as in hormonal regulation (sterols), photosynthesis (carotenoids and others), just to mention a few.

In living cells, IPP can be generated by either the mevalonate-dependent (hereinafter MEV) pathway or the mevalonate-independent or MEP pathway, which are two distinct pathways. Most organisms rely exclusively on one of the pathways for generation of isoprenoid compounds, but plants and some microorganisms have both pathways. The precursor for synthesis of IPP via the MEV pathway is acetyl-CoA, which is synthesized in the central carbon metabolism. The precursors for synthesis of IPP via the MEP pathway are the glycolytic intermediates glyceraldehyde-3-phosphate (GAP) and pyruvate (PYR), which are synthesized in the central carbon metabolism. Both the mevalonate pathway and the MEP pathway produce dimethylallyl diphosphate (DMAPP) and IPP, and the reaction steps after IPP to produce geranyl diphosphate (GPP), farnesyl diphosphate (FPP) and geranylgeranyl diphosphate (GGPP) are the same in cells using either the mevalonate pathway, the MEP pathway or both. It is from these intermediates that the various isoprenoid compounds in nature are produced.

The chemical industry, which produces organic molecules by traditional chemical processes, is increasingly turning to production processes utilizing microbial cell factories. The key drivers for this development towards green chemistry are that such so-called "biotechnological processes" are more environmentally friendly, that many compounds produced by microorganisms are too complex to be obtained by organic synthesis and that the microbial cell factory represents an unlimited supply of the particular compound. Currently, isoprenoids are produced at large scale by extraction from plants or by chemical synthesis. The major drawbacks of both of these methods are low yields and high costs. A third option is to produce the desired isoprenoids by in vitro enzymatic conversion, but this approach is limited by the availability of precursors, and therefore in most cases not economically viable.

Metabolic engineering of microorganisms for isoprenoid production may lead to production of large amounts of isoprenoids from cheap carbon sources in fermentation processes, and thereby solve many of the current problems in industrial isoprenoid production (Maury et al., 2005, Adv. Biochem. Engin/Biotechnol. 100:19), whilst allowing for biotechnological exploitation of the large diversity found in the isoprenoid group of natural compounds.

A number of isoprenoid products have been produced by genetically engineered microorganisms, including limonene (Carter et al., 2003, Phytochem. 64:425), carotenoids (Kajiwara et al, 1997, Biochem. J. 324: 421), epi-cedrol (Jackson et al, 2003, Org. lett 5: 1629), taxadiene (Huang et al, 2001, Biorg. Med. Chem 9: 2237), and others. In order to enhance isoprenoid production in E. coli, the genes dxs (encoding DXP synthase), dxr (DXP reductoisomerase) and idi (IPP isomerase) have been overexpressed with good results for several of the above-mentioned isoprenoid products (reviewed in Maury et al., 2005). A further increase in amorphadiene production by E. coli has been obtained by expressing the mevalonate pathway from S. cerevisiae in an amorphadiene producing strain of E. coli (Martin et al., 2003, Nat. Biotechnol. 21:796). Some isoprenoid compounds have also been produced in yeasts, including epi-cedrol in S. cerevisiae (Jackson et al., 2003, Org. Lett. 5:1629), lycopene and beta-carotene in S. cerevisiae (Yamano et al., 1994, Biosci. Biotechnol. Biochem. 58:1112) and Candida utilis (Miura et al., 1998, Appl. Environ. Microbiol. 64:1226). In several cases, isoprenoid production in yeast has been shown to be enhanced by overexpression of HMG1 (encoding HMG-COA reductase) (reviewed in Maury et al., 2005).

In spite of the background depicted above, there is still a need for further processes for producing terpenes and terpenoids and, in particular, for ways of accumulating terpenes in microorganisms with higher yields and in a less costly and time intensive manner than in the prior known methods. It is therefore an objective of the present invention to provide a method for producing terpenes or terpenoids that fulfils this need.

It is a further objective of the present invention to solve the problem of the supply of sufficient amounts of terpene precursors in an organism so as to enhance the accumulation of terpenes in the organism.

It is a particular objective of the present invention to produce a microorganism that accumulates and/or secretes high amounts of terpenes to the surrounding medium. The production of terpenes by such a microorganism is preferably stable over time.

Still a further objective underlying the present invention is to provide a biological platform for the production of terpenes, which is capable of producing any terpene at the choice of the manufacturer. Such a single system would in principle enable the production of one specific terpene at a time, but could be easily modified to produce another terpene or a mixture of terpenes. The same system could be used, of course, to produce different terpenes independently. Moreover, such a platform could also allow the production of terpene-derived compounds which are useful for the flavour and fragrance industry. One particular example which is not limitative of the invention is the production of nootkatone from valencene.

Furthermore, the biological production platform for terpenes of the invention preferably has high production capacity and is free of endotoxins and all the problems associated with them.

A further objective of the present invention is to provide a biological production platform highly capable of accumulating high levels of lipophilic compounds, even in a generally aqueous medium where such compounds, or their precursors, are not usually soluble.

SUMMARY OF THE INVENTION

Remarkably, the present inventors successfully and stably transformed a microorganism with a heterologous MEP-pathway. The microorganism does not possess a MEP pathway for the production of terpenes in its natural state and is engineered to acquire such a pathway. The microorganism exhibits high production of a terpene compound of choice during cultivation of the microorganism in a suitable medium. Surprisingly, the transformed microorganism is capable of producing increased amounts of any selected terpene as compared to its capability, before such a transformation, to produce said terpene.

Accordingly, in a first aspect, the present invention provides a eukaryotic microorganism having a heterologous MEP-pathway for converting 1-deoxy-D-xylulose 5-phosphate (DXP) to isopentenyl diphosphate (IPP) and/or dimethylallyl diphosphate (DMAPP).

The term "heterologous metabolic pathway" is defined herein as a metabolic pathway which is introduced into the wild type microorganism to produce the recombinant microorganism, a metabolism which was not present in the natural genome of the wild type microorganism, i.e., which was not "native" to that microorganism naturally.

The preferred microorganism of the invention is a fungus, more particularly a yeast of the *Saccharomyces* genus.

The prior art is silent as regards the transformation of a microorganism as presently claimed. Funguses and yeasts present in nature are devoid of the MEP-pathway for the production of terpenes. They produce terpenes via a mevalonate dependent pathway which does not use 1-deoxy-D-xylulose 5-phosphate (DXP) as a precursor of IPP and/or DMAPP.

The introduction of a mevalonate-dependent pathway in a bacterium, which may or may not naturally possess one, has been described by K. Reiling et al. in WO 2005/033287 A1. These authors also suggest generally the possibility of modifying yeast cells to integrate therein DXP pathway enzymes. This document is however entirely silent as regards the manner in which such a transformation can be achieved and does not therefore provide any teaching useful to arrive at the present invention. In fact, without specific teaching of the manner in which such a transformation is achieved, it is impossible to predict the outcome of such an attempt. The MEP-pathway involves a large number of enzymes, each specific to only one particular substrate, and the introduction of all the enzymes together, in a stable manner, so as to provide a recombinant microorganism capable of producing increased amounts of IPP and/or DMAPP, and thus increased amounts of the desired terpenes, is very difficult to achieve. The present inventors provide herein a surprising solution to this problem.

In WO 00/01649 A1, J. Millis et al. suggests that it may be possible to introduce into strains of *Saccharomyces cerevisiae* two enzymes of the *E. coli* MEP-pathway, the dxs and dxr genes. Again, there is no specific description of the manner in which this can be achieved and there is even a disconcerting statement to the effect that the MEP precursor possibly obtained from such a transformation may then be further metabolized by the engineered microorganism via endogenous enzymes—yet, it is known that *Saccharomyces cerevisiae* does not possess such endogenous enzymes and, without specific guidance to this effect, it is apparent what the authors had in mind. It is clear however that no such transformation was realized and it is not apparent how it would be possible to realize in the manner suggested.

Other prior art, represented for example by documents WO 02/18617 A2 and WO 02/083720 A2, has taught how to transform microorganisms comprising a native MEP-pathway for the production of terpenes, but concentrating on amplification or transformation of the native MEP-pathway by overexpression of some of the enzymes involved or other methods making it possible to amplify the native pathway in order to increase terpene or carotenoid production.

To the best of our knowledge therefore, there has never been taught in the prior art a eukaryotic microorganism transformed as is presently claimed.

The present invention also provides a method for accumulating a terpenoid in the cell and/or the medium of a microorganism, the method comprising the step of engineering the microorganism to comprise a heterologous pathway for producing IPP and/or DMAPP.

In a still further aspect, the present invention provides a method for producing a terpenoid, the method comprising the step of cultivating the microorganism of the invention in a medium conducive to the production of said terpenoid, and isolating the terpenoid from the medium and/or the microorganism.

The present invention further provides a method for preparing a microorganism capable of accumulating and/or producing a terpene, the method comprising the step of transforming a microorganism naturally devoid of a MEP-pathway for the production of terpenes, with genes of a heterologous MEP-pathway and at least one gene encoding a terpene synthase.

In another aspect, the present invention provides a method of increasing the amount of terpenoid-precursors in a microorganism, the method comprising the step of transforming a microorganism naturally devoid of a MEP-pathway for the production of terpenes with genes of a heterologous M EP-pathway.

The present invention further relates to a plasmid. Accordingly, the present invention provides a plasmid comprising at least three genes of the MEP-pathway. The invention further provides a plasmid comprising at least three genes of the MEP-pathway and a terpene synthase. Following preferred embodiments, the invention provides a plasmid comprising four enzymes of the MEP-pathway. In yet further specific aspects of the invention, there are provided two plasmids, one plasmid comprising four genes of the MEP-pathway, namely from *E. coli*, and the other plasmid comprising three genes of the MEP-pathway and a terpene synthase.

The invention further relates to the methods of use of such plasmids to transform a eukaryotic microorganism devoid of a native MEP-pathway. The term "native" is used here to refer to a MEP-pathway that is present in the microorganism as found in nature.

The enzymes encoded by the different genes are: dxs: DXP synthase, dxr: DXP reductoisomerase, ispD: MEP cytidylyltransferase, ispE: CDP-ME kinase, ispF: MECDP synthase, gcpE: MECDP reductase, lytB: HMBPP reductase, idi: IPP isomerase.

Figure 2:
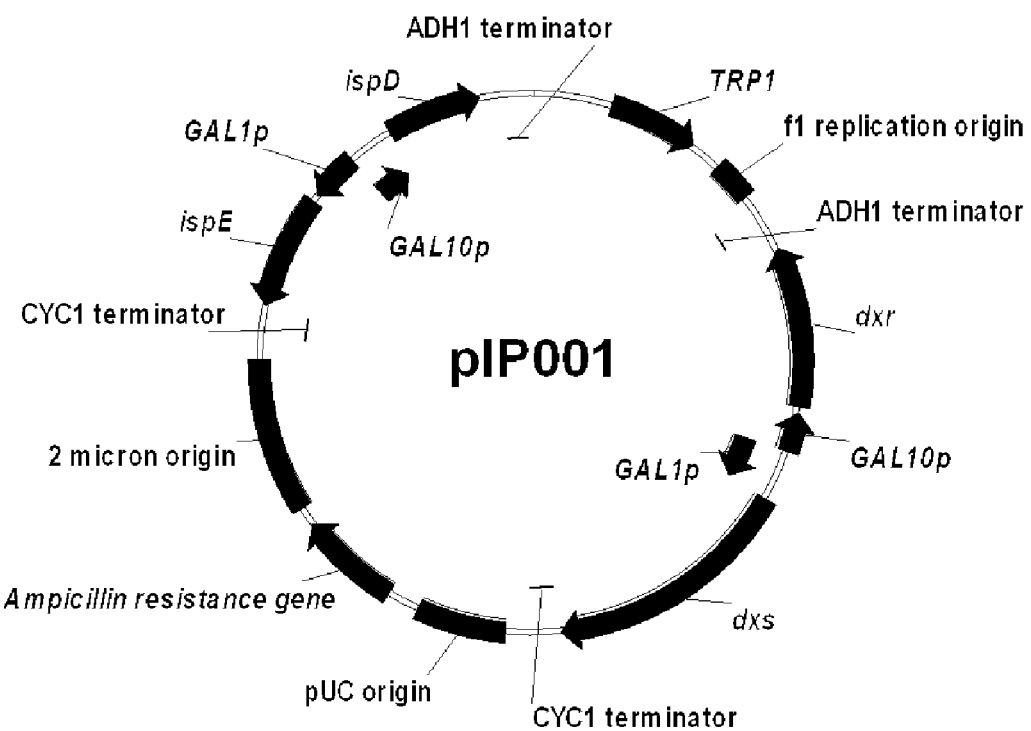
Figure 2:
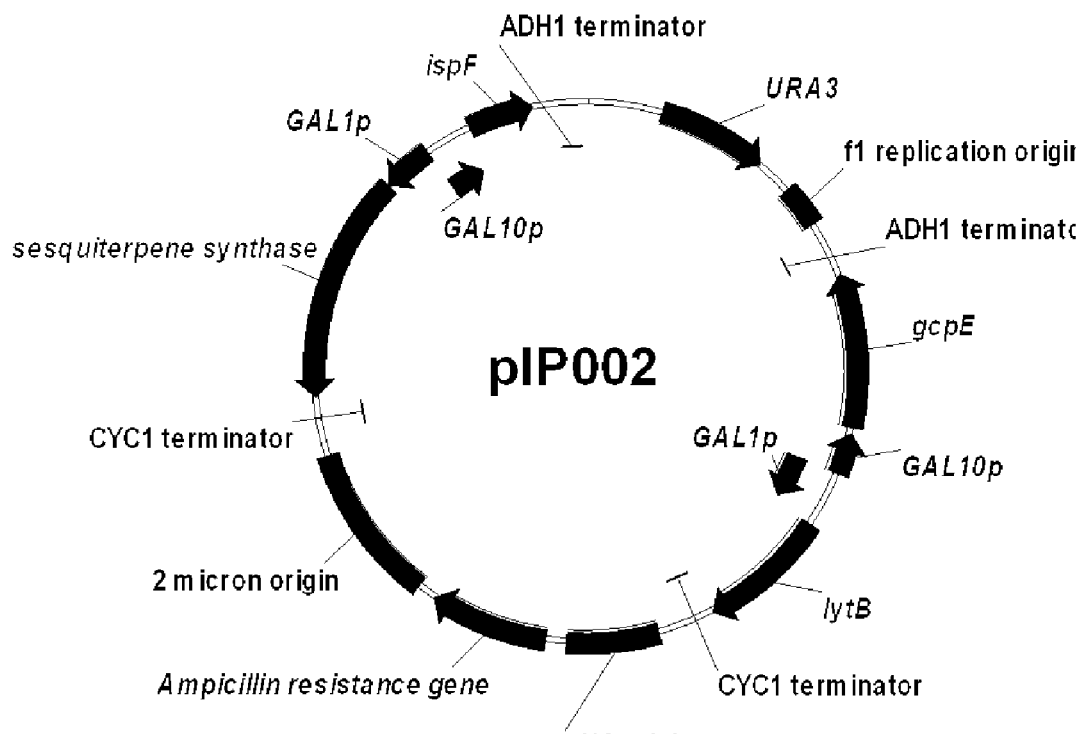

FIG. 2 shows two plasmids pIP001 and pIP002, each plasmid comprising four heterologous sequences of terpene pathways. In particular, pIP001 comprises four genes of the E. coli MEP pathway (dxs, dxr, ispD, ispE), and pIP002 comprises three genes of the MEP pathway (ispF, gcpE, lytB) and a terpene synthase.

Figure 3:
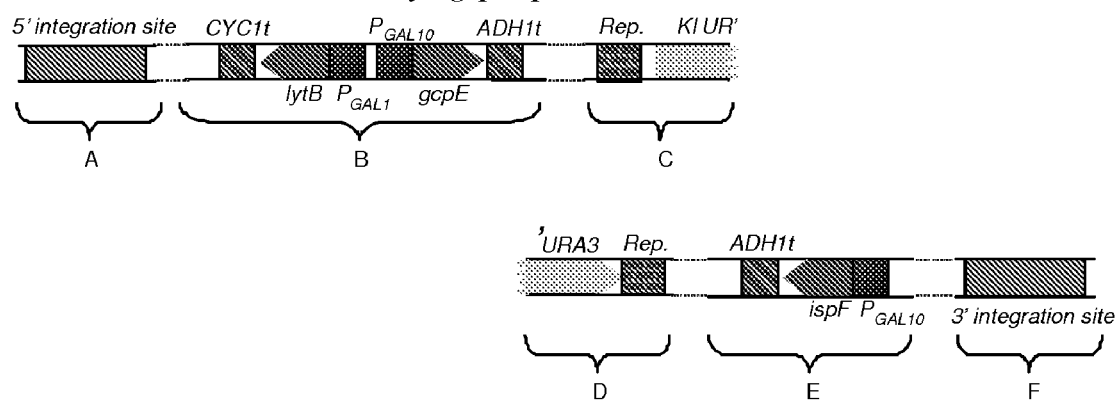
Figure 3:
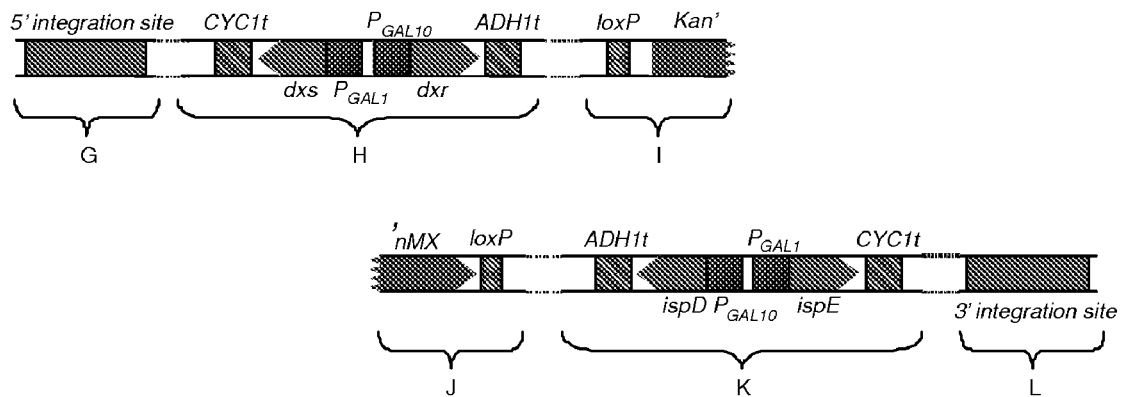

FIG. 3 shows the targeted integration of MEP pathway genes by homologous recombination in S. cerevisiae.

The different fragments, i.e. the fragments A to L, are amplified by PCR. Subsequently, specific fragments are fused together during 2 sequential fusion PCR to finally obtain fragments A/B/C, D/E/F, G/H/I and J/K/L. Fragments A and F provide the required homologous regions for genomic integration of cluster lytB/gcpE/ispF while fragments G and L provide the necessary homologous regions for genomic integration of cluster dxs/dxr/ispD/ispE. Fragments A/B/C and D/E/F are transformed together into S. cerevisiae to obtain targeted insertion of cluster lytB/gcpE/ispF. Fragments G/H/I and J/K/L are transformed together into S. cerevisiae to obtain targeted integration of cluster dxs/dxr/ispD/ispE thanks to in vivo homologous recombination.

Figure 4:
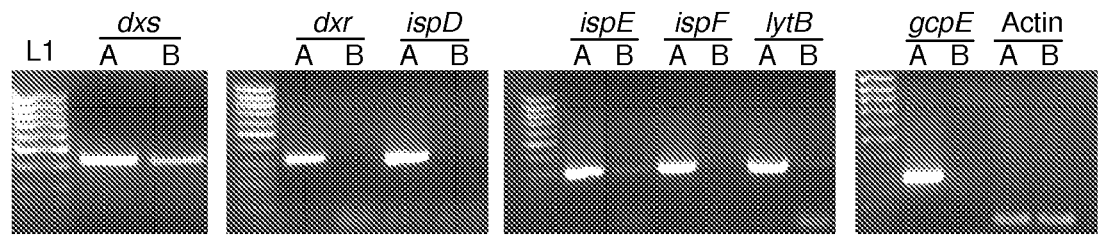

FIG. 4 shows the evaluation of the expression of the MEP pathway genes.

A: sample from strain YIP-DV-02, B: sample from strain YIP-0V-02. Actin gene is used here as internal standard.

Figure 5:
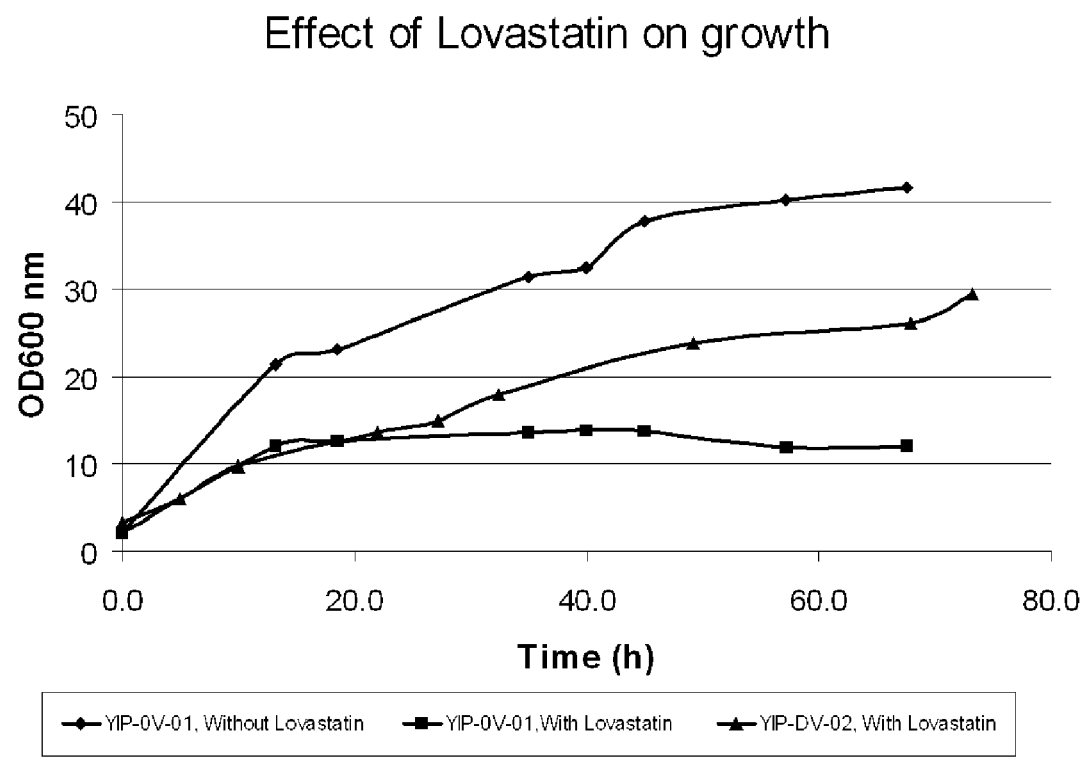

FIG. 5 shows the effect of lovastatin on growth of a yeast strain harbouring MEP pathway and valencene synthase gene (YIP-DV-02) and yeast strain with only valencene synthase gene as control (YIP-0V-01).

Figure 6:
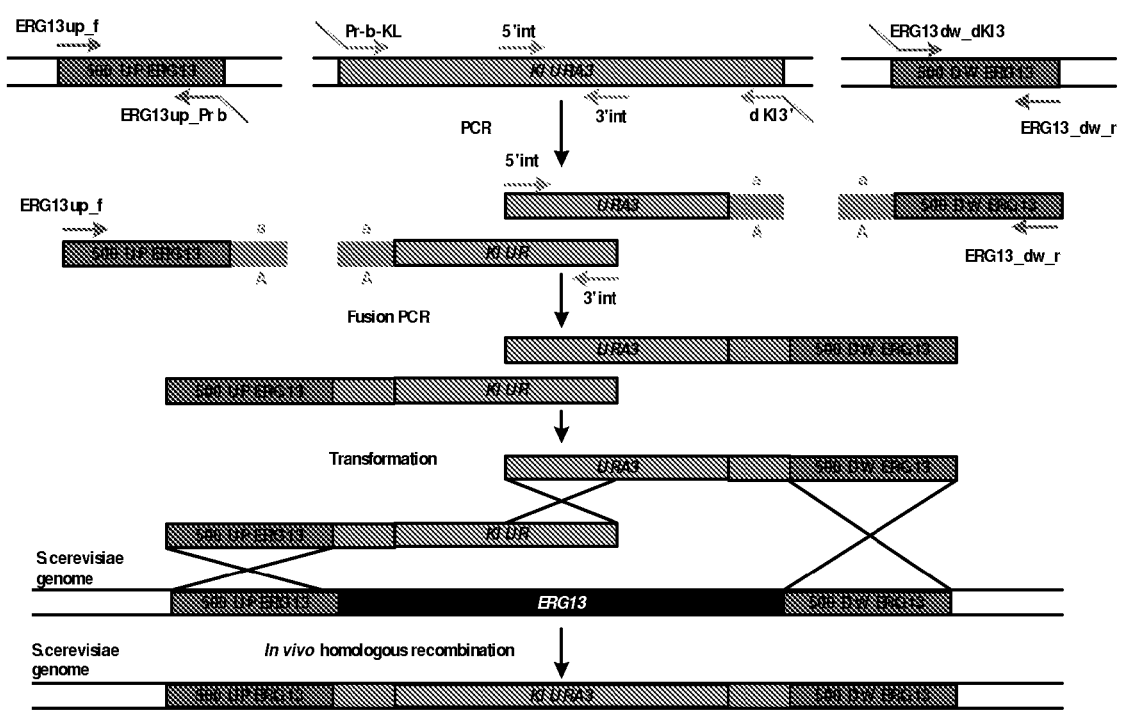

FIG. 6 shows the strategy for the deletion of ERG13 using the selective marker KI URA3. KI URA3 flanked by direct repeats is amplified from pWJ1077 in two separate, but overlapping, fragments using primers having at their extremities adaptamers. Approximately 500 bp fragments upstream and downstream from the insertion site are separately amplified as well by PCR using S. cerevisiae genome as template. Fusion PCR allows the combination of the four PCR fragments into two. These latter are transformed into S. cerevisiae and the KI URA3 construct is integrated at the ERG13 locus thanks to in vivo homologous recombination.

Figure 7:
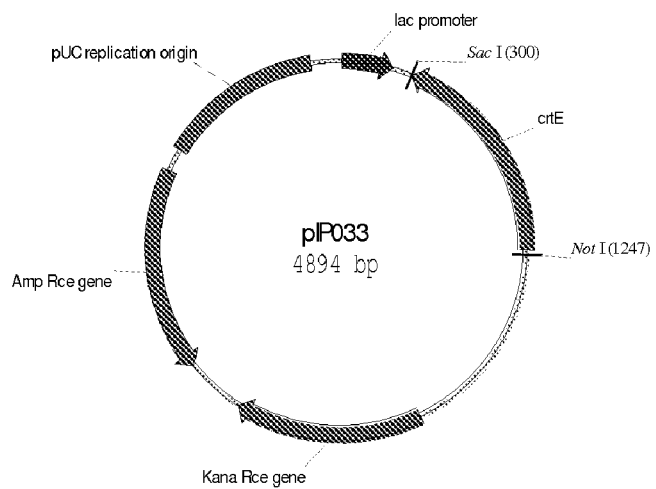
Figure 7:
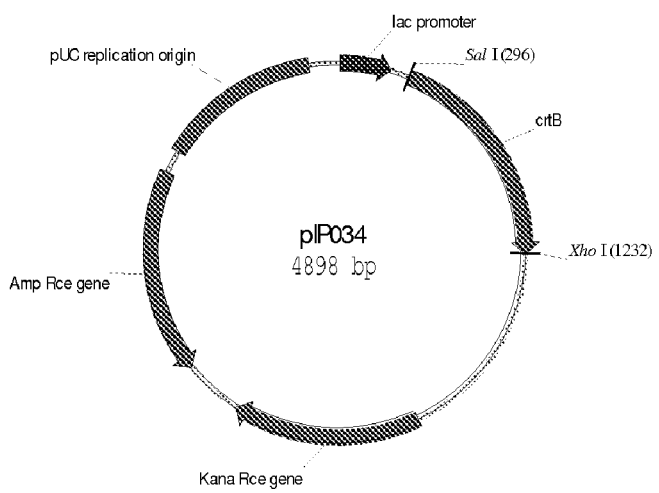
Figure 7:
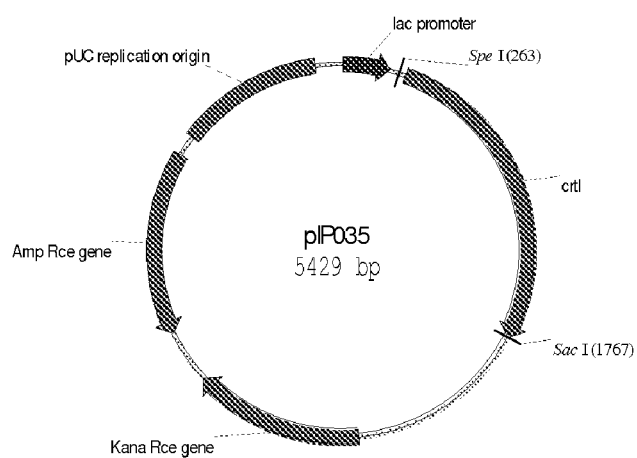

FIG. 7 shows three plasmids used in the construction of a lycopene producing strain of S. cerevisiae, pIP033, pIP034 and pIP035, each plasmid harbouring one of the three codon optimized crt genes from E. herbicola in pCR4TOPO.

Figure 8:
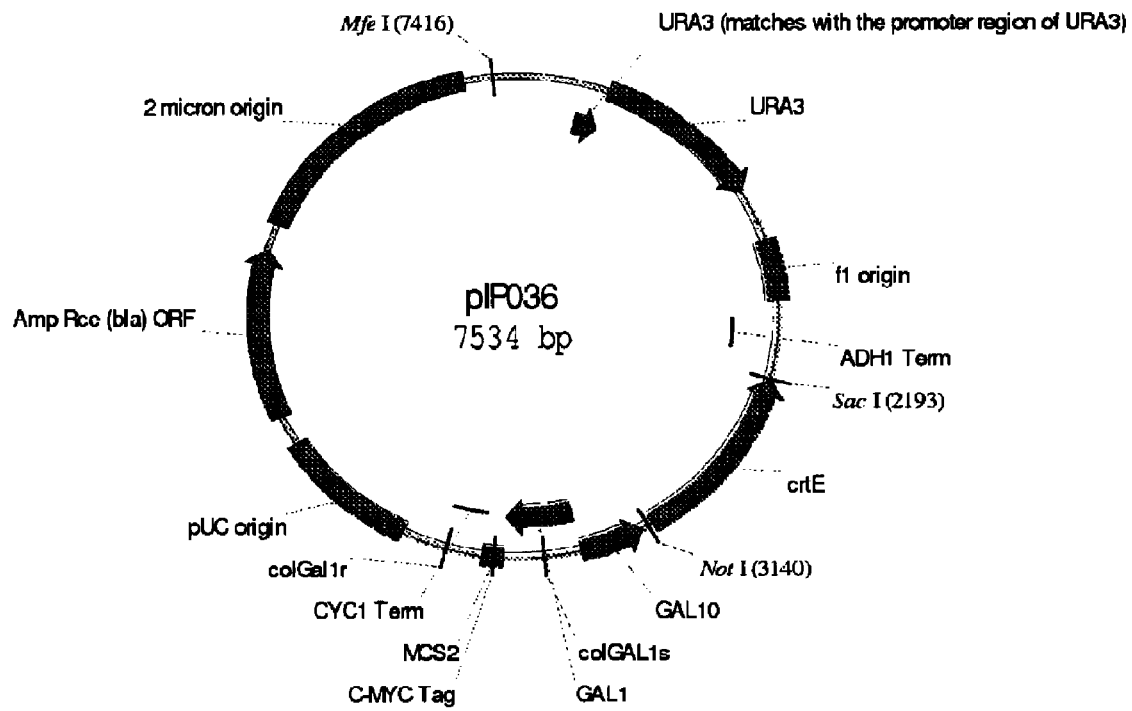
Figure 8:
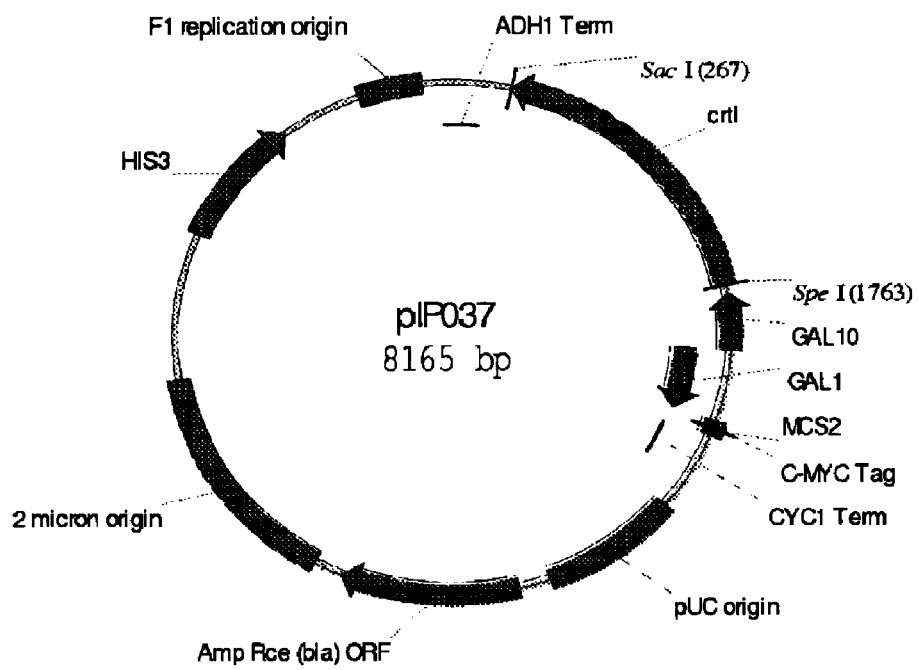
Figure 8:
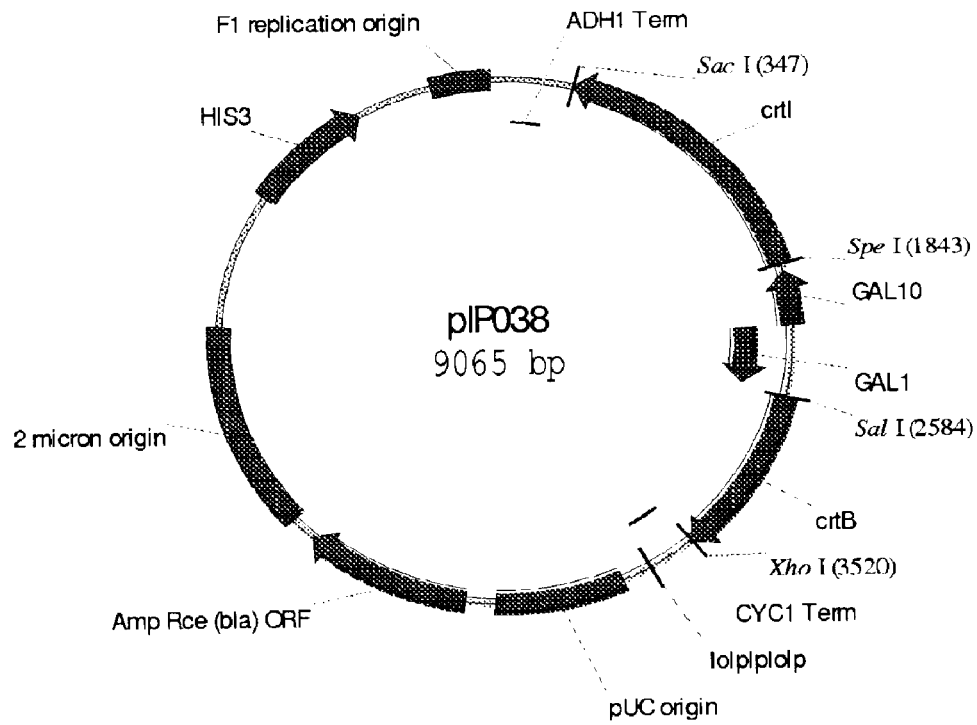
Figure 8:
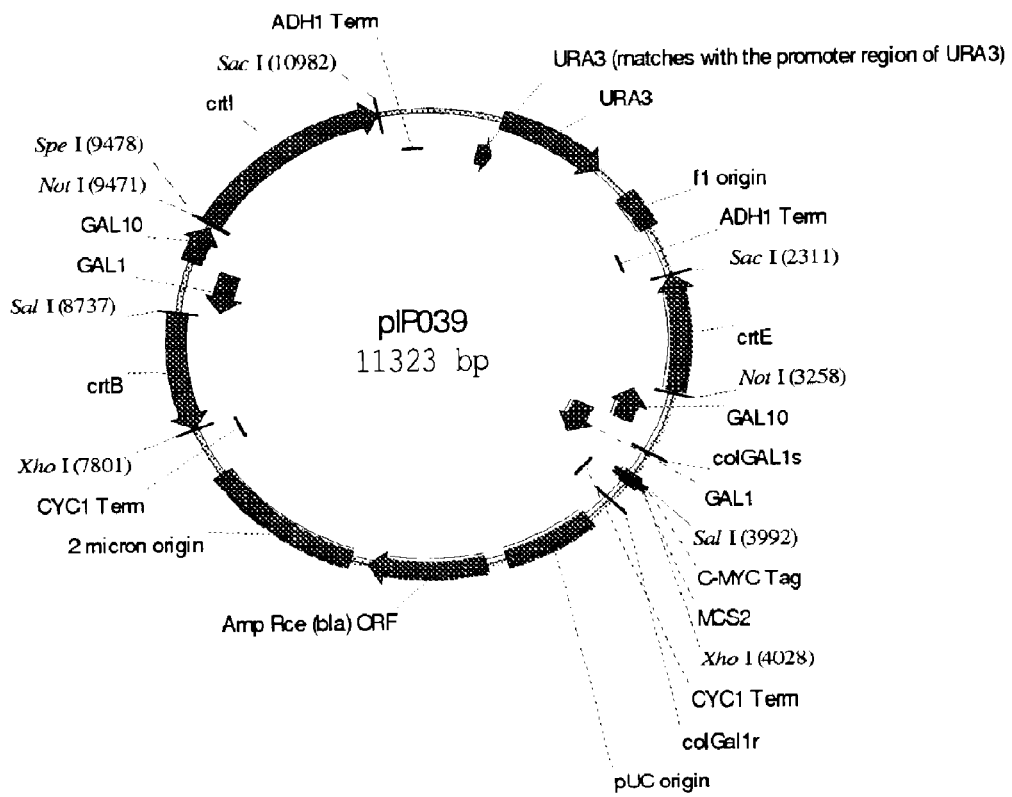

FIG. 8 shows four plasmids used in the construction of a lycopene producing strain of S. cerevisiae, pIP036 (pESC-URA with crtE), pIP037 (pESC-HIS with crtI), pIP038 (pESC-HIS with crtI and crtB), and pIP039 (pESC-URA with crtE, crtB, and crtI), each plasmid harbouring one or more of the three codon optimised crt genes from E. herbicola in pESC-URA or pESC-HIS vectors.

DETAILED DESCRIPTION OF THE INVENTION

The present invention relates to and makes use of a eukaryotic microorganism having a heterologous pathway.

According to preferred embodiments of the invention, the microorganism is a fungal microorganism, more particularly a yeast.

A non-exhaustive list of suitable microorganisms will include the following: a species belonging to the genera Saccharomyces, e.g. S. cerevisiae, S. bayanus, S. pastorianus, S. paradoxus, S. exiguous, S. servazzi, S. uvarum, S. kluyveri, S. castellii, a species belonging to the genera Kluyveromyces, e.g. K. lactis, K marxianus var. marxianus, K. thermotolorens, K. waltii, K. delphensis, K. nonfermentas, K. wickerhamii, a species belonging to the genera Candida, e.g. C. utilis, C. tropicalis, C. castellii, C. humilis, a species belonging to the genera Zygosaccharomyces, e.g. Z. rouxii, Z. bailii, Z. fermentati, Z. bisporus, Z. florentinus, a species belonging to the genera Pichia, e.g. P. stipidis, P. pastoris, P. sorbithophila, P. anomala, or other species, e.g. Hansenula polymorpha, Yarrowia lipolytica, Debaromyces hansenii, Schizosaccharomyces pombe, Torulaspora delbueckii, Ashbya gossipie, Aspergillus niger, Aspergillus awamori, Aspergillus oryzae, Aspergillus nidulans, Penecillium chrysogenum, Rhizopus oryzae, Mucor circenelloides.

More preferably, the microorganism is a yeast and even more preferably, the microorganism is Saccharomyces cerevisiae. For example, it is the S. cerevisiae strain deposited at DSMZ-Deutsche Sammlung von Mikroorganismen und Zellkulturen GmbH. Mascheroder Weg 1b, D-38124 Braunschweig, Germany, accession number: DSMZ 17900, on Jan. 27, 2006.

A heterologous pathway, for the purpose of the present invention, is a pathway which, in its activity to form a compound by defined intermediate steps and from defined starting materials, is not present in the wild-type of the microorganism. More preferably, the heterologous pathway is a pathway derived from DNA of a different species.

The heterologous pathway is the MEP-pathway (2-C-Methyl-D-Erythritol 4-Phosphate-Pathway). This pathway, in a preferred embodiment of the present invention, is capable of converting 1-deoxy-D-xylulose 5-phosphate (DXP) to isopentenyl diphosphate (IPP) and/or dimethylallyl diphosphate (DMAPP). Of course, this capacity refers to in vivo conditions, where any co-factors, minerals etc necessary for the pathway to operate are present.

According to a preferred embodiment of the present invention, the heterologous MEP-pathway is capable of converting glyceraldehyde-3-phosphate (GAP) and pyruvate to IPP and/or dimethylallyl diphosphate (DMAPP).

According to a preferred embodiment, the microorganism of the invention comprises heterologous genes encoding at least one functional enzyme selected from the group of 1-deoxy-D-Xylulose 5-phosphate (DXP) synthase, 1-deoxy-D-Xylulose 5-phosphate (DXP) reductoisomerase, 2-C-methyl-D-erytritol 4-phosphate (MEP) cytidylyltransferase, 4-diphosphocytidyl-2-C-methyl-D-erythritol (CDP-ME) kinase, 2-C-methyl-D-erythritol 2,4-cyclodiphosphate (MECDP) synthase, 2-C-methyl-D-erythritol 2,4-cyclodiphosphate (MECDP) reductase, and 1-hydroxy-2-methyl-2-(E)-butenyl-4-diphosphate (HMBPP) reductase.

For the sake of convenience and simplicity, the term "gene", for example as used in the expression "heterologous genes", is used for designating any nucleotide sequence containing information encoding a protein as specified. Accordingly, the term "gene" is also used for referring to DNA of organisms other than bacteria, such as plants or animals, for example, which generally contains non-coding parts such as introns, or yet where the non-coding parts have been removed. This term is also used for example to refer to cDNA.

Preferably, the microorganism exhibits enzymatic activity of one, some or all the enzymes cited in the above paragraph. More preferably it exhibits activity of all the enzymes of the MEP-pathway.

Figure 1:
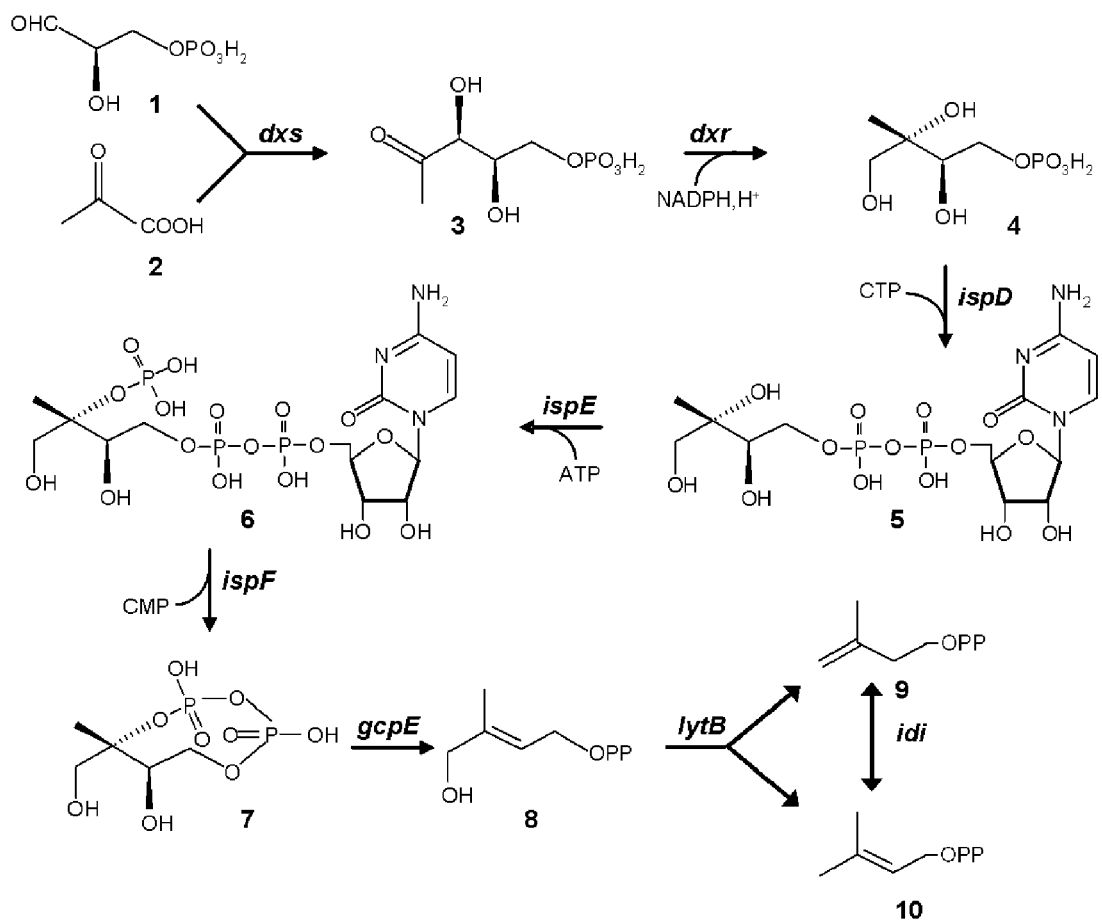
FIG. 1 shows the MEP pathway of *E. coli* for the synthesis of IPP and DMAPP. 1: D-glyceraldehyde 3-phosphate, 2: pyruvate, 3: 1-deoxy-D-xylulose 5-phosphate (DXP), 4: 2-C-methyl-D-erythritol 4-phosphate (MEP), 5: 4-diphosphocytidyl-2-C-methyl-D-erythritol (CDP-ME), 6: 2-phospho-4-diphosphocytidyl-2-C-methyl-D-erythritol (CDP-ME2P), 7: 2-C-methyl-D-erythritol 2,4-cyclodiphosphate (MECDP), 8: 1-hydroxy-2-methyl-2-(E)-butenyl 4-diphosphate (HMBPP), 9: isopentenyl diphosphate (IPP), 10: dimethylallyl diphosphate (DMAPP).

For the purpose of the present invention, these enzymes have the capacity of catalysing the reactions depicted in FIG. 1. For example, DXP synthase is an enzyme having the capacity of catalysing the formation of DXP from D-glyceraldehyde-3-phosphate and pyruvate.

The term "functional", for the purpose of the present invention, refers to the fact that activity of the enzyme can be observed and or deducted in any way. For example, functionality of the heterologous MEP-pathway may be deduced from the presence of IPP in a microorganism devoid of any other pathway for producing IPP than the heterologous one.

The term functional also refers to the fact that the heterologous genes mentioned herein are actually expressed by the microorganism.

For example, the microorganism may have a deletion in its wild-type pathway rendering the native pathway incapable of producing IPP. Under these circumstances, functionality of the heterologous pathway may be deduced from the microorganism's capacity of producing IPP, and thus surviving. For example, if the microorganism is a *S. cerevisiae* strain, a deletion may be constructed in an essential gene of the MEV pathway, for example the ERG13 gene. A deletion cassette may be generated as disclosed in the prior art, with primers comprising overhangs for homologous recombination to delete the essential MEV gene. A viable strain comprising such a deletion is generally proven to depend on the heterologous pathway.

In a preferred embodiment, however, the microorganism has a functional, basically wild-type, MEV pathway and a functional, basically heterologous, MEP pathway. The MEV pathway is defined to be a pathway capable of converting Acetyl-CoA and Acetoacetyl-CoA to IPP and/or DMAPP.

Examples and preferred embodiments of enzymes of the MEP-pathway are those with the following EC numbers: DXP synthase: EC 2.2.1.7; DXP reductoisomerase: EC 1.1.1.267; MEP cytidylyltransferase: EC 2.7.7.60; CDP-ME kinase: EC 2.7.1.148; MECDP synthase: EC 4.6.1.12; MECDP reductase: EC 1.17.4.3; and HMBPP reductase: EC 1.17.1.2.

Heterologous genes encoding these enzymes are disclosed in public databases and are thus available to the skilled person. Examples of such genes of the MEP-pathway are those of *E. coli*. These specimens have the following accession numbers: dxs: (AAC73523, GI:1786622, U00096.2); dxr: (AAC73284, GI:1786369, U00096.2); ispD: (AAC75789, GI:1789104, U00096.2); ispE: (AAC74292, GI:1787459, U00096.2); ispF: (AAC75788, GI:1789103, U00096.2); gcpE: (AAC75568, GI:1788863, U00096.2); lytB: (AAC73140, GI:1786212, U00096.2), for example.

In a preferred embodiment, the microorganism comprises heterologous genes encoding a functional DXP-reductoisomerase (dxr), MEP cytidylyltransferase (ispD), CDP-ME kinase (ispE), MECDP synthase (ispF), MECDP reductase (gcpE) and HMBPP reductase (lytB). Preferably, the microorganism further comprises a heterologous gene encoding a DXP synthase (dxs).

Preferably, the microorganism comprises a heterologous gene encoding a IPP isomerase (idi in FIG. 1).

Preferably, the microorganism comprises a heterologous gene encoding a FPP synthase. Genes encoding IPP isomerases and FPP synthases have been described and are available to the skilled person. Heterologous copies of these genes may be useful to further increase terpene productivity of the microorganism of the present invention.

In a preferred embodiment, the microorganism comprises at least one heterologous gene encoding a functional terpene synthase. An important advantage of the microorganism of the present invention is its suitability to produce any terpene at the choice of the skilled person. Accordingly, any known terpene synthase encoding sequence can be used to be heterologously expressed in the microorganism. The particularity of the present invention resides in the fact that the enzyme functionality of the MEP-pathway results in heterologous production of IPP, while the terpene synthase may be an enzyme capable of converting the precursors indicated below into any terpene.

The term terpene synthase encompasses enzymes, complexes, and/or groups of enzymes capable of synthesising a terpene from one or several precursors. In particular, precursors for terpenes, for the purpose of the present invention, are farnesyl diphosphate (FPP), geranyl diphosphate (GPP), geranylgeranyl diphosphate (GGPP), and any combination of two or more of these.

Preferably, a terpene synthase is a single, complex and/or group of enzymes capable of synthesising a terpene from the precursors GPP, FPP, GGPP or a combination of at least two of these.

A terpene is a saturated or unsaturated, optionally substituted hydrocarbon based on, or composed essentially of, isoprene units (C5). Terpenes may be acyclic or cyclic. Terpenes, as used herein include terpenes, terpene derivatives, and compounds referred to as terpenoids, which may or may not fall in one of the two foregoing classes of compounds. Terpene derivatives include compounds that have undergone one or more steps of functionalization such as hydroxylations, isomerizations, oxido-reductions or acylations, for example. Preferably, for the purpose of the present invention, a terpene is a compound which fulfils the above condition and/or whose carbon skeleton originates, at least in part but preferably totally, from the MEP and/or MEV pathway. Accordingly, terpenes include terpene alcohols, for example $C_{15}H_{26}O$ and $C_{10}H_{18}O$ compounds such as patchoulol, epi-cedrol, cubebol, linalool, nerolidol, for example, and dialcohols, for example sclareol. Terpenes also include diphosphate compounds such as bornyl-diphosphate (monoterpene) and copalyl-diphosphate (diterpene), just to mention a few specimen of the vast category of terpenes.

As used herein, a "derivative" is any compound obtained from a known or putative compound and containing essential elements of the parent substance.

For example, terpenes are compounds having carbon skeletons of $C_{10}$, $C_{15}$, $C_{20}$, $C_{30}$, $C_{40}$, $C_{45}$ and so forth.

Accordingly, the term terpene encompasses mono, sesqui, di, tri, tetra and/or polyterpenes. In a preferred embodiment of the invention, the terpene synthase is a mono, sesqui and/or diterpene synthase. Preferably, it is a sesquiterpene synthase.

According to a preferred embodiment, the terpene of the present invention is a sesquiterpene. For example, the sesquiterpene is cubebol, patchoulol, farnesene, amorphadiene and/or valencene. The genes encoding synthases for these terpenes are available in public databases, for example under the accession numbers AY508730, CQ813505, AY566286, AY523409, DQ309034, AF024615, AF374462, AF138959, AY006482, CQ813508.

Terpene synthases and the genes encoding them are widely available to the skilled person and can be selected according to preferences. A few, non-limiting examples are monoterpene synthases, for example the limonene synthases (L13459, D49368, AAM53944), pinene synthases (AF543530, AF543528), sabinene synthase (AF051901), bornyldiphosphate synthase (AF051900), 1,8-cineol synthase (AF051899) and linalool synthase (AF154124, U58314). Examples for diterpene synthases with available sequences are casbene synthase (P59287), taxadiene synthase (U48796) and abietadiene synthase (U50708). These examples only serve for illustration of the wide applicability of the present invention. Sequences yet to be isolated encoding terpene synthases may equally be employed for working the principle of the present invention.

Preferably, the terpene synthase is heterologous. Accordingly, the terpene is not produced by the native and/or wild-type microorganism. However, the present invention also encompasses instances where the microorganism already comprises a native and/or wild-type gene encoding a synthase for producing a terpene. In this case, the microorganism of the invention comprises further copies of the same gene, or heterologous genes encoding a terpene synthase capable of producing the same terpene or a different one. In that way, higher amounts of that same terpene or a mixture of that terpene with different ones may be produced.

According to a preferred embodiment, the microorganism of the invention provides a yield of at least 30 μg, more preferably at least 100 μg of terpene per g dry-weight of the microorganism. The terpene yield of a microorganism is preferably established by the protocol in Example 10.

Preferably, the heterologous genes are under the control of promoters. Preferably, these promoters are in close vicinity of the heterologous genes. Even more preferably, each of the heterologous genes, that is, those of the MEP pathway, and the terpene synthase gene are each individually under the control of a promoter located upstream of the respective coding sequence. Any promoter may be used, for example strong and/or weak constitutive promoters or inductive promoters. Examples of preferred promoters are the galactose inducible S. cerevisiae promoters such as GAL1 and GAL10, or strong constitutive S. cerevisiae promoters such as TPI1 and TEF1.

Preferably, each of the above mentioned heterologous genes is associated with a terminator sequence. Preferably, the terminator sequence is located downstream of the heterologous gene. As for the promoter sequences, terminator sequences may be selected from a vast pool of terminator sequences known or still to be described. Examples are the S. cerevisiae terminators of CYC1, ADH1, TPI1 or FBP1.

The microorganism may or may not comprise further heterologous genes. Typically, further heterologous genes include marker sequences, such as resistance or auxotrophic markers, indicating that a heterologous gene of choice is present in a selected microorganism.

One problem underlying the present invention is the stabilisation of a high amount of heterologous genetic material over successive generations of the microorganism. Large plasmids are difficult to construct and are not easily taken up and maintained by the microorganism. Furthermore, maintaining plasmids can constitute an energetic cost for the cell, and this can lower the production capabilities. If many small plasmids are used, however, some of them may be lost with each replication cycle. Furthermore, homologous regions on different plasmids, or within the same plasmid, may recombine, resulting in loss of heterologous genetic material.

Remarkably, the present inventors could transform a microorganism by stably introducing a heterologous pathway. The genes of the heterologous pathway can be present on plasmids of the microorganism.

Accordingly, the present invention provides a plasmid and/or a pair of two plasmids as defined hereunder with respect to the microorganism. These plasmids are surprisingly suitable to transform a microorganism with a heterologous MEP-pathway. Preferably, the microorganism comprises at least two plasmids with genes of the heterologous pathway and optionally a gene encoding a terpene synthase. More preferably, it comprises two (2) plasmids.

In a preferred embodiment, the microorganism comprises at least two plasmids, one plasmid comprising at least three (3) and the other plasmid comprising other three (3) genes of the heterologous pathway. Preferably, all genes are different genes having different enzymatic activity.

Accordingly, the present invention provides a plasmid comprising 3 genes of the heterologous pathway, optionally further comprising at least one heterologous gene encoding a functional DXP synthase. More preferably the plasmid comprises 4 genes of the MEP pathway.

The present invention further provides a plasmid comprising 3 genes of the heterologous pathway and further comprising at least one heterologous gene encoding a functional terpene synthase.

Accordingly, the micro-organism preferably comprises two plasmids, one comprising four (4) different genes of the heterologous pathway, including a gene encoding a DXP synthase, and the other plasmid comprising three (3) genes of the MEP-pathway and a gene encoding a terpene synthase.

In a preferred embodiment of the invention, the microorganism comprises at least two (2) plasmids which, taken together, comprise the genes dxs, dxr, ispD, ispE, ispF, gcpE, lytB, and a gene encoding a terpene synthase. In other words, the at least two plasmids, for example 3 or 4 plasmids, comprise these genes so that each gene is present at least on one of the at least two plasmids.

Any suitable vector and/or plasmid may be used for harbouring the heterologous genes. Examples of suitable plasmids for transforming the microorganism are pESC-vectors (e.g. pESC-URA, Stratagene), pYES-vectors (e.g. pYES2/CT, Invitrogen), and pRS-vectors (e.g. pRS426, Sikorski and Hieter, 1989, Genetics 122:19).

According to a preferred, alternative, embodiment, the genes encoding the heterologous pathway, are integrated into the genome of the microorganism.

This embodiment has various advantages compared to the embodiment where the heterologous pathway genes are located on plasmids. First, integration into the genome increases the stability of the integration of the heterologous genes over successive generations. Furthermore, subsequent optimisation procedures, such as evolutionary engineering, are much easier to realize. Then, this system is more flexible with respect to the localisation of the gene encoding the terpene synthase. The latter may then be present on a comparatively small plasmid and/or also integrated into the genome. Basic advantages of the integration into the genome are thus stability, and, to a lesser extent, flexibility.

Accordingly, in a preferred embodiment, the heterologous pathway genes and/or the DXS synthase gene are integrated in the genome of the microorganism, and a gene encoding a terpene synthase is present on a plasmid and/or integrated in the genome. Preferably, the gene encoding a terpene synthase is present on a plasmid as this facilitates further transformation of the microorganism with a variety of synthases.

Alternatively, the heterologous terpene synthase gene may be inserted into the genome of the microorganism, and the heterologous MEP-pathway genes and/or the DXP synthase gene be present on plasmids as disclosed above, for example.

Further possible variations relating to the repartition of heterologous genes in the genome and/or the plasmids will be appreciated by the skilled person and are not discussed in every detail.

The genome of the microorganism, for the purpose of the present invention, is equivalent to the totality of chromosomal DNA, but excludes DNA of plasmids and mitochondrial DNA.

All heterologous DNA may be codon-optimized. Accordingly, codons of heterologous DNA are preferably modified to correspond to the preferred codons of the microorganism. Codons may also be modified to minimize the GC content of heterologous DNA and alter secondary structure formation of the mRNA. This allows to obtain higher levels of MEP pathway enzymes and/or terpene synthase, heterologously expressed in the microorganism.

Ergosterol is an essential compound for the growth of certain microorganisms, such as fungi, and in particular yeast. However, in order to draw carbon flux towards the production of the terpene of choice according to the invention, ergosterol production in the microorganism of the invention is preferably reduced. This is preferably achieved by replacing promoters of ergosterol biosynthesis with only weakly constitutive and/or repressible promoters. Preferably, the native promoter of the squalene synthase encoding gene ERG9 in yeast is replaced by a weakly constitutive or a repressible promoter. For example, in yeast, the native promoter may be replaced by the MET3 promoter of S. cerevisiae. Promoters may be replaced by fusion PCR and the bipartite gene targeting method (Ederniz et al., 1997, Genome Research 7: 1174).

If the microorganism is a fungus, and preferably a Saccharomyces strain, phosphatases hydrolysing important intermediates for terpene accumulation like FPP and/or GGPP are preferably totally or partially inactivated. In S. cerevisiae, products of the genes LPP1 (YDR284C) and DPP1 (YDR284C) were shown to have such activity (Faulkner et al, 1999, J. Biol. Chem. 274: 14831). These or similar genes are thus preferably deleted if present in the microorganism of the present invention.

The present invention provides methods for accumulating a terpene in the cell and/or medium of a microorganism, for producing a terpene and for increasing the amount of terpene precursors in a microorganism.

The terpenes may accumulate in the cells. For example, they may accumulate in the cytoplasm, in mitochondria, cellular membranes or other cell organelles. Many terpenes are lipophilic compounds, which accumulate in the plasma membrane of the cell.

For the purpose of the present invention, the term "accumulating in the medium" also encompasses accumulation in a solvent during a two-phase fermentation process.

The terpene and the microorganism used in such methods are as defined above. The medium of the microorganism may be liquid or solid at 25° C. (room temperature), but is preferably liquid.

The medium is selected as a function of the needs of the selected microorganism. The medium thus contains all ingredients and factors necessary for growth and/or production of the terpene. Often, a different medium is selected for growth of the microorganism than for production of the terpene. The latter is usually achieved by bringing the microorganism to a stage in its life-cycle where replication is minimized and transcription and/or protein synthesis maximized. The medium generally needs to contain all factors necessary for the at least short term survival of the strain.

According to a preferred embodiment, the step of cultivating the microorganism and/or the step of isolating the terpene from the medium is performed via a two-phase fermentation.

Accordingly, immiscible and biocompatible organic solvents are added to a cultivation medium.

These solvents form a second, preferably hydrophobic phase, capable of accumulating the terpene and/or avoiding its loss through evaporation or other phenomena. In this way, the organic solvents may be used for in-situ separation of metabolites in fermentation (Frenz et al., 1989, Enzyme Microb. Technol. 11:717; Sim et al., 2001, Biotechnol. Lett. 23:201). A two-phase fermentation, for the purpose of the present invention, is a method of cultivating a microorganism characterised by the presence of at least one organic solvent in, or in addition to, the medium of the microorganism, to form at least a two-phase system.

Preferably, the organic solvent does not significantly affect growth and/or survival of the microorganism. Suitable solvents for two-phase fermentations are diisononyl phthalate, dibutyl phthalate, oleyl alcohol, dihexyl ether and dodecane, for example.

The two-phase fermentation thus also includes an at least partial separation and/or isolation of the terpene from the medium.

The method for accumulating a terpene comprises the step of engineering the microorganism to comprise the heterologous MEP-pathway for producing IPP and/or DMAPP. The engineering may be performed on the basis of the material described above. Accordingly, the engineering may be by transformation with plasmids and/or by genomic integration of heterologous genetic material. The procedures for genetic engineering are known to the skilled person and no limitation with respect to any particular methodology is necessary.

According to a preferred embodiment, the method comprises the step of engineering the microorganism to comprise a heterologous terpene synthase. Preferably, the step of engineering is performed by transforming the microorganism to comprise plasmids comprising genes encoding enzymes of the heterologous pathway.

In a further embodiment, the method comprises the step of cultivating the microorganism under conditions conducive to the production of said terpene. These conditions are known to the skilled person. Generally, they may be adjusted by selection of an adequate medium, fermentation vessel, temperature, and pH.

The method for producing a terpene may comprise the step of isolating the terpene from the medium, from the cells and/or from an organic solvent, in case a two-phase fermentation is performed. The terpene may be isolated by any method used in the art including but not limited to chromatography, extraction and distillation, for example.

The microorganisms and methods according to the invention thus provide an improved and flexible platform for the production of a variety of individual terpenes, or mixtures thereof, and this platform may be further complemented via possible further transformation of the microganisms via integration or amplification of other enzymes capable of converting the terpenes into other compounds useful in the flavor and fragrance industry in particular. One obvious such use is for the conversion of appropriate terpenes into carotenoids, via integration of the appropriate enzymes into the microorganisms of the invention, via plasmid or genome incorporation. Another is the conversion of valencene into nootkatone for example, by further insertion in the microorganism metabolism of a cytochrome P450 monooxygenase capable of effecting this conversion. The invention thus provides a useful and advantageous tool for production of terpenes and their derivatives, as well as precursors therefore.

EXAMPLES

The following examples are intended to illustrate the invention without limiting the scope as a result. The percentages are given on a weight basis unless otherwise indicated.

Examples 1-4

Genes dxs, dxr, ispD, ispE, ispF, gcpE and lytB genes were amplified from E. coli genomic DNA by PCR using the primers listed in Table 1.

Terpene synthases encoding genes, in particular, genes encoding patchoulol synthase (PatTps177, GeneBank accession No. AY508730), cubebol synthase (GFTpsC, GenBank accession No. CQ813505) and valencene synthase (GFTpsD, GenBank accession No. CQ813508) were amplified from plasmid pET11a or pET101 containing these genes and using the primers listed in Table 4. The sequences of these terpene synthases, as well as the isolation of the respective genes, and the construction of the above mentioned plasmids are disclosed in WO05/052163, WO05/056803 (patchoulol synthase) and WO04/031376 (valencene and cubebol synthase).

The PCR conditions were in accordance with the Expand High Fidelity standard conditions (Roche Applied Science). The DNA fragments were separated by gel electrophoresis and the fragments of expected size then purified using the High Pure PCR Product Purification Kit (Roche Applied Science).

Examples 1-4, Part (a)

The purified PCR products of the dxr, ispD, ispF, lytB, valencene synthase gene and cubebol synthase gene and a plasmid (pESC-TRP or pESC-URA) were digested with the restriction enzymes indicated in Table 1 or 4 and purified with the QIAEX® II Gel extraction kit (Qiagen). For terpene synthase genes, pESC-TRP was used, otherwise see Table 1. In vitro ligation of the digested plasmid with the digested PCR product was performed as the standard procedure given for T4 DNA ligase (Roche Applied Science) with an insert/vector ratio of at least 3:1 and incubated at 4° C. for 16 hours. The resulting ligation mix was used to transform chemically competent E. coli cells (DH5α) (Inoue et al, 1990, Gene 96:23) and transformants were selected on LB medium supplemented with ampicillin (1% Tryptone, 0.5% yeast extract, 1% NaCl, 2% agar, pH 7, 75 mg/L ampicillin).

Transformants were then verified by purifying plasmids and performing digestion with suitable restriction enzymes. If a transformant contained a plasmid of the correct size, 1 μg of the plasmid DNA was purified and sent for sequencing.

The plasmids obtained are as follows:
dxr in pESC-TRP: pIP020; ispD in pESC-URA: pIP018; ispF in pESC-TRP: pIP016; lytB in pESC-URA: pIP009; Valencene synthase in pESC-TRP: pIP027; Cubebol synthase in pESC-TRP: pIP013.

TABLE 1

PCR primers used for cloning E. coli pathway genes

| Genes | Primers | Sequence | Cloning technique | Original plasmid |
| --- | --- | --- | --- | --- |
| dxr | dxrM1A | ggactagtcctaatgaagcaactcaccattc | SpeI | pESC-TRP |
|  | dxrM1B | ccatcgatggTCAGCTTGCGAGACGCATC | ClaI |  |
| dxs | dxsGAPs | ACTTTAACGTCAAGGAGAAAAAACCCCGGAT CCCatgagttttgatattgcc | GAP repair |  |
|  | dxsGAPr | TTCTTCGGAAATCAACTTCTGTTCCATGTCG ACGCCTTATGCCAGCCAGGCCTTG | GAP repair |  |
| ispD | ispDM1A | GGACTAGTCCTAatggcaaccactcatttgg | SpeI | pESC-URA |
|  | ispDM1B | CCATCGATGGTTATGTATTCTCCTGATGG | ClaI |  |
| ispE | isPEGAPs | ACTTTAACGTCAAGGAGAAAAAACCCCGG ATCCCatgcggacacagtggccctc | GAP repair |  |
|  | ispEGAPr | TTCGGAAATCAACTTCTGTTCCATGTCGACG CCTTAAAGCATGGCTCTGTGCAATGG | GAP repair |  |
| ispF | ispFM1A | ggactagtcctaatgcgaattggacacgg | SpeI | pESC-TRP |
|  | ispFM1B | ccatcgatggTCATTTTGTTGCCTTAATG | ClaI |  |
| gcpE | gcpEM1A | GGACTAGTCCTAatgcataaccaggctccaa ttc | SpeI | pESC-URA + lytB |
|  | gcpEM1B | CGAGCTCGTTATTTTTCAACCTGCTGAACG | ClaI |  |
| lytB | lytBM1A | GCGTCGACGTCTTGatgcagatcctgttggc caacc | SalI | pESC-URA |
|  | lytBM1B | CCCTCGAGGGTTTAATCGACTTCACGAATAT CG | XhoI |  |
| "Fusion" | pfus_grf | CAGCACTACCCTTTAGCTGTTCTATATGCTG CCACTCCTacgcaaaccgcctctccccg | GAP repair |  |
|  | Pfus_grr | AGGAAATGATAGCATTGAAGGATGAGACTAA TCCAATTAtcggtgcgggcctcttcgc | GAP repair |  |

The "cloning technique" involves either digestion of templates by cited restriction enzymes followed by ligation and transformation of the resulting products into E. coli, or in vivo construction thanks to GAP repair in S. cerevisiae.

Examples 1-4, Part (b)

The remaining genes, dxs, ispE, gcpE and a selected terpene synthase where inserted each to one of the aforementioned plasmids (pIP020, 018, 009) by classic cloning or the gap repair method as follows.

The gcpE, valencene synthase and cubebol synthase PCR products were cloned following the scheme below:

TABLE 2

| PCR-product | Cloning plasmid | Resulting plasmid |
|---|---|---|
| gcpE | pIP009 (lytB in pESC-URA) | pIP008 |
| Valencene synth. | pIP016 (ispF in pESC-TRP) | pIP015 |
| Cubebol synth. | pIP016 (ispF in pESC-TRP) | pIP014 |

PCR products and plasmids were digested with the restriction enzymes indicated in Table 1 or Table 4, respectively, purified, in vitro-ligated, followed by transformation of E. coli, selection of transformants and verification of transformants by sequencing of expected plasmids exactly as indicated for Examples 1-4(a) above.

The gap repair method was used to clone dxs into pIP020, ispE into pIP018 and a patchoulol synthase into pIP016 to obtain plasmids each comprising two additional genes.

This cloning method utilizes homologous recombination in yeast to join homologous DNA sequences (DeMarini et al, 2001, BioTechniques 30:520-52). This technique consists in generating PCR products with extremities homologous to the insertion site on the plasmid to construct. The primers utilized for cloning dxs, and ispE are given in Table 1, those for cloning a terpene synthase in Table 4.

PCR products (dxs, ispE, terpene synthase) and target plasmids were digested according to the following scheme:

TABLE 3

| PCR-product, | Cloning plasmid | Restr. Enzymes | Resulting plasmid |
|---|---|---|---|
| dxs | PIP020 | BamHI and SalI | pIP019 |
| IspE | PIP018 | SalI | pIP017 |
| Patchoulol synt. | pIP016 | XmaI | PIP012 |

Digested PCR-product and plasmid were both transformed in S. cerevisiae YIP-00-02 (MATa trp1 ura3) using standard transformation procedure (Gietz and Woods, 2002, Methods in Enzymology 350: 87). Transformants were selected on SC-trp medium (6.7 g/L yeast nitrogen base without amino acids, 2 g/L minus trp drop out mix, 2% glucose, 2% agar) or SC-ura medium (6.7 g/L yeast nitrogen base without amino acids, 2 g/L minus ura drop out mix, 2% glucose, 2% agar). After 2-3 days of incubation at 30° C., all the transformants were inoculated in a single test tube containing 5 mL of SC-trp (6.7 g/L yeast nitrogen base without amino acids, 2 g/L minus trp drop out mix, 2% glucose) or SC-ura (6.7 g/L yeast nitrogen base without amino acids, 2 g/L minus ura drop out mix, 2% glucose) and incubated 12 h at 30° C. From this cultivation total DNA was isolated (Sambrook and Russell, 2000, Molecular cloning a laboratory manual $3^{rd}$ ed. 6.31-6.32) and utilized afterwards to transform chemically competent E. coli cells (DH5α) (Inoue et al, 1990). Transformants were selected on plates containing LB medium supplemented with ampicillin.

TABLE 4

| Genes | Primers | Sequence | Cloning technique |
|---|---|---|---|
| Cubebol s. | GFTps CM2A | CGGGATCCCGTGGGCCCTatggca cttcaagattcaga | BamHI |
| | GFTps CM2B | AAGACGTCGACGCTTCAAAAGGGA ACAGGCTTCT | SalI |
| Valencene s. | GFTps D6M2A | cgggatcccgtgggccctatgtcg tctggagaaacatt | BamHI |
| | GFTps D6M2B | aagacgtcgacgctTCAAAATGGA ACGTGGTCTC | SalI |
| Patchoulol s. | Ps_GA P_f | ACTTTAACGTCAAGGAGAAAAAAC CCCGGATCCAATGGAGTTGTATGC CCAAAGTGTTG | Gap repair |
| | Ps_GA P_r | TTCTTCGGAAATCAACTTCTGTTC CATGTCGACGCCTTAATATGGAAC AGGGTGAAGGTACAAC | Gap repair |

The "cloning technique" involves either digestion of templates by cited restriction enzymes followed by ligation and transformation of the resulting products into E. coli, or in vivo construction thanks to GAP repair in S. cerevisiae.

Example 5

Plasmid Combination by in vivo Homologous Recombination in Saccharomyces cerevisiae (Gap Repair)

To reduce plasmid instability and facilitate further integration of the genes in Saccharomyces cerevisiae genome, the 4 plasmids were combined together, two by two, to end up with 2 main plasmids: one bearing dxs, dxr, ispD, ispE (pIPO01) and the other bearing gcpE, lytB, ispF and a sesquiterpene synthase gene (in the case of valencene synthase, this plasmid is named pIP002). Combination of the different plasmids was realized by gap repair in S. cerevisiae (DeMarini et al, 2001, BioTechniques 30:520-52).

To construct plasmid pIP002, the piece of DNA containing ispF, valencene synthase encoding gene, GAL1 and GAL10 promoters, CYC1 and ADH1 terminators (pIPO15) was amplified by PCR using the primers pfus_grf and pfus_grr (Table 1). The resulting PCR products were purified using the High Pure PCR Product Purification Kit (Roche Applied Science). The plasmid pIP008 (pESC-URA containing gcpE and lytB) was digested by MfeI, and subsequently purified after gel electrophoresis using QIAEX® II Gel Extraction Kit (Qiagen). The purified and digested plasmid together with the PCR products were used in the transformation of S. cerevisiae YIP-00-03 (MATa ura3) (Gietz and Woods, 2002). The transformants were selected on plates containing SC-ura medium. After 2-3 days of incubation at 30° C., all the transformants were inoculated in a single test tube containing 5 mL of SC-ura and incubated 12 h at 30° C. From this cultivation total DNA was isolated (Sambrook and Russell, 2000) and utilized afterwards to transform chemically competent E. coli cells (DH5α) (Inoue et al, 1990). Transformants were selected on plates containing LB medium supplemented with ampicillin. Transformants were then verified by purifying plasmids and performing enzymatic digestion with suitable restriction enzymes. In the case of transformants containing the expected plasmid, 1 μg of plasmid DNA was purified and sent for sequencing. The resulting plasmid pESC-URA containing gcpE, lytB, ispF and valencene synthase was named pIP002 (FIG. 2).

The same protocol was followed to construct plasmid pIP001, i.e. the piece of DNA containing ispD, ispE, GAL1 and GAL10 promoters, CYC1 and ADH1 terminators was amplified by PCR using the primers pfus_grf and pfus_grr (Table 1). The resulting PCR products were purified using the High Pure PCR Product Purification Kit (Roche Applied Science). The plasmid pESC-TRP containing dxs and dxr was digested by XcmI, and subsequently purified after gel electrophoresis using QIAEX® II Gel Extraction Kit (Qiagen). The purified and digested plasmid together with the PCR products were used in the transformation of S. cerevisiae YIP-00-02 (MATa trp1 ura3) (Gietz and Woods, 2002). Transformants were selected on plates containing SC-trp medium. After 2-3 days of incubation at 30° C., all the transformants were inoculated in a single test tube containing 5 mL of SC-trp and incubated 12 h at 30° C. From this cultivation total DNA was isolated (Sambrook and Russell, 2000), and utilized afterwards to transform chemically competent E. coli cells (DH5α) (Inoue et al, 1990). Transformants were selected on plates containing LB medium supplemented with ampicillin. Transformants were then verified by purifying plasmids and performing enzymatic digestion with suitable restriction enzymes. In the case of transformants containing the expected plasmid, 1 μg of plasmid DNA was purified and sent for sequencing. The resulting plasmid pESC-TRP containing dxs, dxr, ispD and ispE was named pIP001 (FIG. 2).

The protocol above for producing plasmid pIP002 was repeated by replacing pIP015 by pIP014 and pIP012, to obtain plasmids pIP003 and pIP005 comprising cubebol and patchoulol synthase genes, respectively.

Example 6

Construction of a S. cerevisiae Strain Expressing the MEP Pathway from Plasmids for the Production of Isoprenoids The purified plasmids pIP001 and pIP002 (FIG. 2) were successively transformed (Gietz and Woods, 2002) in the strain S. cerevisiae YIP-00-02 (MATa trp1 ura3). After transformation with pIP001, transformants were selected on plates containing SC-trp medium. A transformant was colony purified and transformed with pIP002. Transformants were selected on plates containing SC-trp-ura medium (6.7 g/L yeast nitrogen base without amino acids, 2 g/L minus trp minus ura drop out mix, 2% glucose, 2% agar). A number of transformants were inoculated in a series of independent test tubes containing 5 mL of SC-trp-ura and incubated 12 h at 30° C. From these cultivations, total DNA was isolated from each transformant (Sambrook and Russell, 2000). The presence of the MEP pathway genes was verified by PCR. Three clones characterized by the presence of the MEP pathway genes and the valencene synthase gene were selected for further characterization and named YIP-DV-01, YIP-DV-02 and YIP-DV-03. YIP-DV-02 was deposited at the DSMZ under deposit number DSM 17900. Each gene encoding each of the 7 enzymes of the MEP pathway was amplified by PCR from the strain YIP-DV-02 and sent for sequencing (MWG-Biotech AG DNA Sequencing Service). The resulting sequences were compared to the original gene sequences of the E. coli MEP pathway genes deposited in Genbank® to verify the absence of mutations.

Construction of S. cerevisiae strains expressing the MEP pathway together with either cubebol synthase or patchoulol synthase encoding genes was realized as described for the construction of S. cerevisiae strains YIP-DV-01, YIP-DV-02 and YIP-DV-03. To construct plasmids containing gcpE, lytB, ispF and a sesquiterpene synthase, the same procedure as in Example 5 was followed but replacing valencene synthase by the appropriate sesquiterpene synthase cited above. These strains, all expressing the MEP pathway and expressing either cubebol synthase or patchoulol synthase are named respectively YIP-DC-01 and YIP-DP-01.

Example 7

Integration of the MEP Pathway Genes in the Saccharomyces cerevisiae Genome

In order to stabilize the expression of the MEP pathway genes, the expression cassettes of the 7 genes were integrated in the genome of Saccharomyces cerevisiae. This is realized using in vivo homologous recombination in Saccharomyces cerevisiae (DeMarini et al, 2001) and bipartite gene targeting method (Ederniz et al, 1997, Genome Research 7: 1174). Integration of the 2 gene clusters is realized in 2 specific loci. The strategy for integration is as follows (FIG. 3). For each gene cluster (dxs/dxr ispD/ispE or gcpE/lytB ispF), 6 PCR products are first generated (FIG. 3) from plasmid pIP001 or pIP002. These PCR products are then fused together during 2 subsequent fusion PCR. For example fragments A, B and C are first amplified separately. Then they are fused during 2 fusion PCR, resulting a long linear A/B/C fragment (FIG. 3) The resulting fused PCR fragments are characterized by overlapping regions at the level of the selective marker (Kluyveromyces lactis URA3 or KanMX) and by extremities sharing homology with the 2 different integration sites on the genome (FIG. 3). The integration sites are the ura3 locus for the first cluster and pDC6 (encoding an isozyme of pyruvate decarboxylase of minor activity) or a non coding region of the genome for the second genome. These characteristics are essential for targeted insertion of the 2 gene clusters in S. cerevisiae genome. PCR is realized according to the Expand High Fidelity standard conditions (Roche Applied Science). PCR products are purified using the High Pure PCR Product Purification Kit (Roche Applied Science) after each PCR and fusion PCR step. The last fragments are used for the transformation of S. cerevisiae YIP-00-03 (MATa ura3) by a standard protocol (Gietz and Woods, 2002). Transformants are selected on plates containing SC-ura medium for the insertion of the cluster lytB/gcpE-KI URA3-ispF and on plates containing SC-ura medium supplemented with geneticin for the insertion of both clusters. After 2-3 days of incubation at 30° C., single colonies are cultivated overnight in 5 mL of SC-ura+geneticin medium (6.7 g/L yeast nitrogen base without amino acids, 2 g.L$^{-1}$ minus ura drop out mix, 2% glucose, 200 mg.L$^{-1}$ geneticin, 2% agar). From this cultivation total DNA is isolated (Sambrook and Russell, 2000). Integration of the gene clusters at specific loci is verified by PCR. One of the selected resulting strains is YIP-D0-01.

Example 8

Evaluation of the Expression of the E. coli MEP Pathway Genes in S. cerevisiae

In order to verify the expression of all the 7 genes of the E. coli MEP pathway in S. cerevisiae, their expression profiles were assessed throughout a fermentation using RT-PCR (Reverse Transcription-PCR). To specifically detect the expression of each MEP pathway gene, a set of specific primers was designed for each of them (Table 5), and the PCR conditions optimized.

While cultivating strains YIP-DV-02 and YIP-0V-02 in shake flasks, using galactose as carbon source (20 g.L$^{-1}$), maintaining cultivation temperature at 30° C. and stirring at 150 rpm, samples were taken in different growth phases and total RNA extracted according to FastRNA® Pro Red kit (Qbiogene). To remove any trace of contaminating DNA, a subsequent treatment of RNA samples with Turbo DNase™ (Ambion) was applied following the standard conditions described for the Turbo DNase-free™ kit (Ambion, Foster City, Calif.). The RNA was then stored frozen at −80° C. After verifying concentration and integrity of the RNA samples, RT-PCR was performed as follows. Reverse transcription for synthesis of the first single-stranded DNA was realized according to Expand Reverse Transcriptase standard conditions (Roche) using primers specific for each MEP pathway gene (Table 6). The reaction was stopped by placing the tubes on ice. Then a PCR reaction was realized using the a Taq DNA polymerase and the primers specific for each gene. The annealing temperatures were 55° C. for dxs, ispD, ispE, ispF and lytB, 57° C. for dxr and gcpE and 53° C. for actin (used as an internal standard). Elongation time was 90 seconds and the amplification was performed during 35 cycles. To confirm that the DNA fragment observed were amplified from mRNA and not from the plasmid DNA, a control PCR was performed in the same conditions as for the RT-PCR but without the reverse transcription step. These control PCR revealed none or minor amounts of contaminating amplification from DNA not affecting the RT-PCR experiment.

TABLE 5

Primers used for assessing the expression of the MEP pathway genes by RT-PCR.

| Genes | Primers | Sequence | Excepted size (bp) | $T_m$ (° C.) |
|---|---|---|---|---|
| dxr | Dxr_f_new | CAGTGATTCACTCAATGGTG | 424 | 58 |
|  | Dxr_r_new | ACGCATCACCTCTTTTCTGGCG |  | 60 |
| lytB | lytB_f | CTGGCAGAACAGGCGGAAGTTG | 299 | 61 |
|  | lytB_r | ACGCAGCTCTTTCGGCACTTC |  | 58 |
| idpF | ispF_f | GCTCCATGCGTTGACCGATG | 302 | 64 |
|  | ispF_r | CCGGTAAATCCCAGTTTTTCCG |  | 58 |
| ispE | ispE_f | TAAAGATCCTGAACTCCCGCGC | 291 | 59 |
|  | ispE_r | CATGGCTCTGTGCAATGGGG |  | 64 |
| ispD | ispD_f | CGCACCAGTGCGCGATACTAT | 298 | 60 |
|  | ispD_r | CCTGATGGATGGTTCGGGTGAG |  | 60 |
| gcpE | gcpE_f | AACTTCATCGCCTGCCCGAC | 300 | 64 |
|  | gcpE_r | CAATTCGACGCGCTTCGTCC |  | 64 |

TABLE 5-continued

Primers used for assessing the expression of the MEP pathway genes by RT-PCR.

| Genes | Primers | Sequence | Excepted size (bp) | $T_m$ (° C.) |
|---|---|---|---|---|
| dxs | dxs_f | TGATGCCAGAAGCGGCGAAAG | 300 | 62 |
|  | dxs_r | TTGGCTTCCATACCAGCGGC |  | 64 |
| ACTIN | Actin_forward | GCCGGTATTGACCAAACTAC | ~200 | 54 |
|  | Actin_reverse | GGTGATTTCCTTTTGCATTC |  | 57 |

For each of the MEP pathway genes, mRNA were specifically detected in S. cerevisiae YIP-DV-02 in a late cultivation phase after galactose exhaustion. No bands were observed in the control strain YIP-0V-02 not transformed with MEP pathway genes (FIG. 4). This experiment clearly shows that the 7 MEP pathway genes are expressed in strain YIP-DV-02.

Example 9

Effect of Lovastatin on Growth in Shake Flasks of S. cerevisiae Expressing the MEP Pathway In order to test the functionality of the MEP pathway in the S. cerevisiae strain harbouring MEP pathway from E. coli, lovastatin (mevinolin) was used as an inhibitor of the mevalonate pathway. However, lovastatin is an inactive lactone, but in the hydrolyzed form it acts as an extremely potent inhibitor of HMG-COA reductase. Lovastatin was hydrolyzed in ethanolic NaOH [15% (v/v) ethanol, 0.25% (w/v) NaOH] at 60° C. in a water bath for 1 h. After cooling, the 20 mg/ml stock solution of lovastatin was filter sterilized and stored at −20° C. for the subsequent use.

Test tubes containing defined minimal medium (Verduyn et al., 1992, Yeast 8:501), different levels of lovastatin and 20 g/L galactose as carbon source were inoculated from a pre-culture to an optical density (OD) at 600 nm of 0.01, and incubated at 30° C. and 150 rpm, and growth was followed by measuring OD (FIG. 5). It was observed that the strain harbouring the MEP pathway and valencene synthase (S. cerevisiae YIP-DV-02) showed better growth in the presence of lovastatin compared to the control strains with only the native mevalonate pathway and valencene synthase (YIP-0V-01). The control strain completely stopped growing after 20 hours at an OD of around 12, whereas the strain expressing the MEP pathway continued to grow for more than 60 hours and reached an OD of around 30 (FIG. 5). This clearly shows that the E. coli MEP pathway is functionally expressed in the strain S. cerevisiae YIP-DV-01.

Example 10

Two-phase Fermentation for in situ Separation of Isoprenoids

For efficiently accumulating hydrophobic and highly volatile terpenes, two-phase fermentation using immiscible and biocompatible organic solvents as the second phase, can be used. Two phase fermentation has been used for in situ separation of some metabolites in fermentations (Frenz et al., 1989, Enzyme Microb. Technol. 11:717; Sim et al., 2001, Biotechnol. Lett. 23:201). In this example, dodecane was used for in situ separation of valencene. The production of valencene by S. cerevisiae expressing the MEP pathway and valencene synthase (YIP-DV-02) was investigated. As a reference, the strain only expressing the valencene synthase (YIP-0V-01) was also cultivated. In the first strain, the valencene synthase is expressed from a galactose inducible promoter, whereas in the latter strain, the valencene synthase is expressed from the constitutive TPI1 promoter. This means that the differences observed in valencene production levels between the strains are both an effect of the MEP pathway and potentially also of the promoter of the valencene synthase.

For the purpose of determining terpene yield per dry matter of microorganism (biomass), the following procedure is applied:

Baffled, cotton stopped, 500 ml Erlenmeyer flasks containing 100 ml of defined minimal medium (Verduyn et al., 1992, Yeast 8:501) and 15 g/L galactose were inoculated, to an optical density (OD) at 600 nm of 0.05, with overnight cultures of either YIP-0V-01 or YIP-DV-02 strains, and incubated at 30° C. and 150 rpm. When OD at 600 nm reached to 1.0, 10 ml of dodecane (equivalent to 10% of the culture media) was added to each shake flask. Dodecane did not show any significant effect on growth (data not shown). At the end of logarithmic phase, once galactose had been depleted, the media was centrifuged and the upper organic phase was analysed by GC-MS for valencene (see below). OD was checked every hour after addition of dodecane. The time of galactose depletion is when OD measurement reveals for the first time that exponential growth is over.

The results are given in Table 6. This experiment proved the possibility of using two-phase fermentation for in situ separation of valencene as a volatile isoprenoid. Table 5 shows that the strain harbouring MEP pathway has accumulated approximately 10 times more valencene compared to the strain expressing only the endogenous mevalonate (MEV) pathway.

TABLE 6

Two-phase fermentation for evaluating valencene production by YIP-0V-01 and YIP-DV-02 strains in batch growth in shake flasks with 15 g/L galactose

| Strain | Valencene conc. (µg/L) | Yield (µg/gDW) | Productivity (µg/L/h) |
|---|---|---|---|
| YIP-0V-01 | 19.5 | 5.3 | 1.2 |
| YIP-DV-02 | 186 | 39.9 | 8.3 |

For the analysis and quantification of the terpene, a combination of mass spectrometry and gas chromatography was used as detailed below:

A Finnigan Focus gas chromatograph equipped with a Finnigan Focus DSQ mass spectrometer and a ZB-5ms capillary column (30 m×250 µm ID×0.25 µm film thickness, Phenomenex) was used for analysis of samples. GC-MS analysis was performed using a GC oven temperature program of 80° C. for 1 min, a ramp of 10° C./min to 130° C. followed by a ramp of 3° C./min to 160° C., and finally a ramp of 10° C./min to 270° C. and keeping the temperature at 270° C. for 5 min. 1 ml/min of helium was applied as carrier gas. The GC-MS was run in the splitless mode for 0.8 min and afterwards the split valve was opened with 50 ml/min split flow.

The biomass was determined as cell dry weight by the use of nitrocellulose filters with a pore size of 0.45 µm (Gelman Sciences, Ann Arbor, Mich.). First, the filters were predried in a microwave oven at 180 W for 10 min, and weighed. A known volume of cell culture was filtered, and then the residue was washed with distilled water. Finally, the filter was dried in the microwave at 180 W for 15 min, and weighed.

The concentration of terpene per biomass was calculated as follows: The corresponding concentration in the 100 ml growth medium given in Table 3 was calculated as $C = 0.01 * C_v / 0.1 = C_v / 10$, with Cv being the concentration of valencene in the dodecane phase established by GC-MS as indicated above. The yield of terpene (valencene) on biomass was calculated as the accumulated valencene concentration divided by the accumulated biomass concentration (from the time of dodecane addition to the time of galactose depletion). Yield=$(C_v/10)/(X_t - X_0)$, where $X_t$ is the biomass concentration at the time of galactose depletion (and valencene quantification), and $X_0$ is the biomass concentration at the time of dodecane addition. The productivity was calculated as the accumulated valencene concentration divided by the time of accumulation. Productivity=$(C_v/10)/(T_t - T_0)$, where $T_t$ is the time of galactose depletion (and valencene quantification), and $T_0$ is the time of dodecane addition.

The experiment showed that valencene was produced by YIP-DV-02 in a yield of 39.9 µg valencene per g dry weight biomass produced, during the exponential phase of aerobic batch growth on galactose. This corresponded to a volumetric productivity of 8.3 µg per L medium per hour (Table 6).

Example 11

Construction of a S. cerevisiae Strain Expressing the MEP Pathway from E. coli and Having a Deletion of an Essential Gene in the Mevalonate Pathway Saccharomyces cerevisiae YIP-00-02 (MATa ura3 trp1) is used to construct a strain with a deletion of an essential gene of the mevalonate pathway, by transformation with a deletion cassette. A deletion cassette for the S. cerevisiae gene ERG13 is generated by PCR amplification of the K.I. URA3 marker from the plasmid pWJ1077 (Reid et al., 2002, Methods Enzymol. 350, 258-277), with primers containing overhangs for a subsequent fusion PCR to the upstream and downstream regions of ERG13 on the S. cerevisiae genome. These regions are obtained by PCR using S. cerevisiae genome as template (FIG. 6 and Table 7). The 4 obtained fragments are combined by fusion PCR to obtain 2 fragments overlapping for part of the K.l. URA3 marker. PCR is realized according to the Expand High Fidelity standard conditions (Roche Applied Science). PCR products are purified using the High Pure PCR Product Purification Kit (Roche Applied Science) after each PCR and fusion PCR step.

TABLE 7

Primers used for deletion of ERG13

| Primer | Sequence |
|---|---|
| ERG13up_f | GACGAACTGGATGAGATGG |
| ERG13up_Pr-b | gatccccgggaattgccatgGAGAGTTTCATGCTGCACC |
| Pr-b-KL | catggcaattcccggggatcGTGATTCTGGGTAGAAGATCG |
| 5'int | CTTGACGTTCGTTCGACTGATGAGC |
| dKI3' | gtcagcggccgcatccctgcCCTCACTAAAGGGAACAAAAGCTG |

TABLE 7-continued

Primers used for deletion of ERG13

| Primer | Sequence |
|---|---|
| 3'int | GAGCAATGAACCCAATAACGAAATC |
| ERG13dw_dKI3' | gcagggatgcggccgctgacCGATTGCATCTTGCTGAACCC |
| ERG13_dw_r | CCAGAGGTCAAATTCCCTC |

Adaptamers are depicted as lower-case letters.

The resulting DNA fragments are used to transform *S. cerevisiae* YIP-00-02 using standard methods (Gietz and Woods, 2002) and thanks to in vivo homologous recombination, ERG13 is deleted. ΔERG13 transformants are selected on SC-ura medium supplemented with mevalonate (50 mg/L), ergosterol (10 mg/L) and Tween80 (0.5%). Correct deletion of ERG13 is verified by diagnostic PCR after total DNA isolation from each transformant (Sambrook and Russell, 2000), and by growth phenotyping in the presence/absence of mevalonate, ergosterol or Tween80. *S. cerevisiae* strain MATa trp1 Δerg13 is obtained and named YIP-M0-06.

Metabolite requirement of *S. cerevisiae* YIP-M0-06 (MATa trp1 Δerg13) can be overcome by introduction of the MEP pathway from *E. coli*, after having looped out K.I. URA3 marker by cultivation on synthetic medium supplemented with 5-fluoro-orotic acid (5-FOA) (6.7 g/L yeast nitrogen base without amino acids, 2 g/L minus ura drop out mix, 50 mg/L uracil, 1 g/L 5-FOA, 2% glucose, 2% agar). By transformation of this strain with either plasmids pIP001 and pIP002, pIP001 and pIP003, pIP001 and pIP004, pIP001 and pIP005, or pIP001 and pIP006, strains YIP-DV-04 (Δerg13 MEP pathway and valencene synthase), YIP-DC-03 (Δerg13, MEP pathway and cubebol synthase), YIP-DC-04 (Δerg13, MEP pathway and codon optimized cubebol synthase), YIP-DP-03 (Δerg13, MEP pathway and patchoulol synthase) and YIP-DP-04 (Δerg13, MEP pathway and codon optimized patchoulol synthase) are obtained, respectively.

Example 12

Construction of a Lycopene Producing Strain of *S. cerevisiae*, Expressing the MEP Pathway from *E. coli*

An ura3 variant of *S. cerevisiae* YIP-D0-01 was first selected by plating this strain on synthetic medium supplemented with 5-fluoro-orotic acid (5-FOA) (6.7 g/L yeast nitrogen base without amino acids, 2 g/L minus ura drop out mix, 50 mg/L uracil, 1 g/L 5-FOA, 2% glucose, 2% agar). The selected YIP-D0-01 (MATa ura3 MEP) strain is used for expression of the genes for lycopene production.

The lycopene biosynthetic genes were derived from the crtE (Genebank accession no. AAA21260), crtB (Genebank accession no. AAA21264) and crtI (Genebank accession no. AAA21263) genes from *Erwinia herbicola* encoding respectively a geranylgeranyl diphosphate synthase, a phytoene synthase and a phytoene desaturase. The nucleotidic sequences of the lycopene biosynthetic genes were modified to optimise their expression in yeast. The codons were modified without changing the aminoacid sequences. The three crt codon optimized genes were synthesized with appropriate restriction sites added at their extremities and primarily cloned in pCR4TOPO plasmid (Invitrogen) and the plasmids bearing crtE, crtB, and crtI genes were named pIP033, pIP034, and pIP035, respectively (FIG. 7).

The crt genes on pCR4TOPO plasmid were digested using restriction enzymes and were subcloned into yeast expression vectors pESC-URA and pESC-HIS (Stratagene). pIP033 and pESC-URA plasmid DNA were digested with SacI and NotI restriction enzymes, and subjected to agarose gel electrophoresis. The resulting fragments were gel purified using GFX Gel Band Purification Kit (Amersham Biosciences), in vitro-ligated, followed by transformation into *E. coli*, selection of transformants and verification of transformants by restriction profile analysis and sequencing. From transformants exhibiting correct ligation of the crtE gene into the pESC-URA vector, the plasmid pIP036 was purified and stored.

pIP035 and pESC-HIS plasmid DNA were subsequently digested with SacI and SpeI restriction enzymes. The resulting fragments were gel purified, in vitro-ligated, followed by transformation into *E. coli*, selection of transformants and verification of transformants by restriction profiling and sequencing. Transformants with correct ligation of the crtI gene into the pESC-HIS vector, were used to purify the plasmid (pIP037).

pIP034 and pIP037 plasmid DNA were subsequently digested with SalI and XhoI restriction enzymes, and the plasmid pIP038 (crtB gene into the pIP037 vector) was obtained in the same manner as indicated before, purified and stored.

To reduce plasmid instability and facilitate further integration of the genes in *S. cerevisiae* genome, the 2 plasmids (pIP036 and pIP38) were combined together in order to obtain plasmid pIP039. Combination of the two plasmids was realized using the gap repair method in *S. cerevisiae* (DeMarini et al, 2001, BioTechniques 30:520-52). To construct plasmid pIP039, the piece of DNA containing crtI, crtB, GAL1 and GAL10 promoters, CYC1 and ADH1 terminators (pIP038) was amplified by PCR using the primers pfus_grf and pfus_grr (Table 1). The resulting PCR product was purified using the High Pure PCR Product Purification Kit (Roche Applied Science). The plasmid pIP036 (pESC-URA containing crtE) was digested by MfeI, and subsequently purified after gel electrophoresis using QIAEX® II Gel Extraction Kit (Qiagen). The purified and digested plasmid together with the PCR products were used in the transformation of *S. cerevisiae* YIP-00-03 (MATa ura3). Transformants were selected on plates containing SC-ura medium. After 2-3 days of incubation at 30° C., all the transformants were inoculated in a single test tube containing 5 mL of SC-ura and incubated 12 h at 30° C. From this cultivation total DNA was isolated and utilized afterwards to transform chemically competent *E. coli* DH5α cells. Transformants were selected on plates containing LB medium supplemented with ampicillin. Transformants were then verified by purifying plasmids and performing enzymatic digestion with suitable restriction enzymes. In the case of transformants containing the expected plasmid, 1 μg of plasmid DNA was purified and sent for sequencing. The resulting plasmid pESC-URA containing crtE, crtB, and crtI genes was obtained and named pIP039. FIG. 8 shows different constructed pESC vector containing crt genes.

A lycopene producing strain of *S. cerevisiae*, expressing the MEP pathway from *E. coli*, is constructed by transforming *S. cerevisiae* YIP-D0-01 (MATa ura3 MEP) with the constructed plasmid pIP039 containing crtE, crtI and crtB. The resulting strain is YIP-DK-01.

INDUSTRIAL APPLICABILITY

The microorganism of the present invention is useful for the production of complex terpene compounds, their precursors and their derivatives.

The invention claimed is:

1. A recombinant fungus of the *Saccharomyces* genus comprising heterologous genes encoding enzymes in a heterologous pathway for converting 1-deoxy-D-xylulose 5-phosphate (DXP) to isopentenyl diphosphate (IPP) or dimethylallyl diphosphate (DMAPP), the native metabolism of the microorganism being devoid of the pathway, such heterologous genes being genes encoding a functional 1-deoxy-D-xylulose 5-phosphate (DXP) synthase, a functional DXP-reductoisomerase, a functional (2-C-methyl-D-erythritol 4-phosphate (MEP) cytidylyltransferase, a functional 4-diphosphocytidyl-2-C-methyl-D-erythritol (CDP-ME) kinase, a functional 2-C-methyl-D-erythritol 2,4-cyclodiphosphate (MECDP) synthase, a functional MECDP reductase and a functional 1-hydroxy-2-methyl-2-(E)-butenyl 4-diphosphate (HMBPP) reductase, said microorganism further comprising a heterologous gene encoding a functional terpene synthase, with all heterologous genes integrated in the genome of the fungus, which is the *Saccharomyces cerevisiae* strain YIP-DV-02 having deposit number DSM 17900.

2. A method for accumulating a terpene in a cell of a culture of the recombinant fungus of claim 1 or in the medium of a culture of the recombinant fungus of claim 1, comprising the step of culturing the recombinant fungus of claim 1.

3. A method for producing a terpene, which comprises cultivating the recombinant fungus of claim 1 in a culture medium while isolating the terpene thus produced in the medium.

4. The method of claim 2, wherein the cultivating of the fungus is performed, at least partially, via a two-phase fermentation.

5. A method for producing a terpene, comprising the steps of:
   (a) culturing the recombinant fungus of claim 1; and
   (b) isolating the terpene produced from the culture medium.

* * * * *

UNITED STATES PATENT AND TRADEMARK OFFICE
CERTIFICATE OF CORRECTION

PATENT NO. : 8,048,658 B2
APPLICATION NO. : 12/279300
DATED : November 1, 2011
INVENTOR(S) : Clark et al.

Page 1 of 1

It is certified that error appears in the above-identified patent and that said Letters Patent is hereby corrected as shown below:

Title Page:
Add the following before Item (51):

-- (30)    Foreign Application Priority Data
   Feb. 14, 2006   (WO) ..................... PCT/IB2006/050476 --

Signed and Sealed this
Sixth Day of December, 2011

David J. Kappos
*Director of the United States Patent and Trademark Office*